US009388454B2

(12) United States Patent
Kamiya et al.

(10) Patent No.: US 9,388,454 B2
(45) Date of Patent: Jul. 12, 2016

(54) METHOD FOR PRODUCING PROTEIN-NUCLEIC ACID CONJUGATE, AND METHOD FOR DETECTING TARGET SUBSTANCE

(71) Applicants: KYUSHU UNIVERSITY, NATIONAL UNIVERSITY CORPORATION, Fukuoka-shi, Fukuoka (JP); HITACHI ALOKA MEDICAL, LTD., Mitaka-shi, Tokyo (JP)

(72) Inventors: Noriho Kamiya, Fukuoka (JP); Kounosuke Hayashi, Mitaka (JP); Kenji Nagai, Mitaka (JP)

(73) Assignees: KYUSHU UNIVERSITY, NAT'L UNIVERSITY CORPORATION, Fukuoka-shi (JP); HITACHI ALOKA MEDICAL, LTD., Tokyo (JP)

( * ) Notice: Subject to any disclaimer, the term of this patent is extended or adjusted under 35 U.S.C. 154(b) by 0 days.

(21) Appl. No.: 14/408,375

(22) PCT Filed: Jun. 14, 2013

(86) PCT No.: PCT/JP2013/067018
§ 371 (c)(1),
(2) Date: Dec. 16, 2014

(87) PCT Pub. No.: WO2013/191265
PCT Pub. Date: Dec. 27, 2013

(65) Prior Publication Data

US 2015/0284762 A1 Oct. 8, 2015

(30) Foreign Application Priority Data

Jun. 22, 2012 (JP) ................................ 2012-141089

(51) Int. Cl.
*C12Q 1/68* (2006.01)
*C12P 19/34* (2006.01)
(Continued)

(52) U.S. Cl.
CPC ............... *C12Q 1/6804* (2013.01); *C12P 19/34* (2013.01); *C12P 21/02* (2013.01); *G01N 33/532* (2013.01); *G01N 33/5308* (2013.01); *G01N 33/58* (2013.01); *G01N 33/582* (2013.01)

(58) Field of Classification Search
CPC .................................................... C12Q 1/6804
USPC ................................................. 435/6.1, 91.1
See application file for complete search history.

(56) References Cited

U.S. PATENT DOCUMENTS 5,986,086 A 11/1999 Brush et al.
6,239,159 B1 5/2001 Brown et al.

(Continued)

FOREIGN PATENT DOCUMENTS

JP 2000-504009 A 4/2000
JP 2001-519354 A 10/2001

(Continued)

OTHER PUBLICATIONS

Balamurugan et al., "Effect of Linker Structure on Surface Density of Aptamer Monolayers and Their Corresponding Protein Binding Efficiency" Analytical Chemistry, vol. 80, No. 24, Dec. 15, 2008, pp. 9630-9634.

(Continued)

*Primary Examiner* — Jezia Riley
(74) *Attorney, Agent, or Firm* — Westerman, Hattori, Daniels & Adrian, LLP

(57) ABSTRACT

Provided is a method for producing a nucleic acid probe that can detect a target substance with good sensitivity. A method for producing a nucleic acid probe, comprising: a 3'-terminal addition step of adding at least one nucleoside triphosphate derivative having a glutamine (Gln) residue or a lysine (Lys) residue to the 3'-terminal of a nucleic acid using a 3'-terminal addition enzyme which adds a nucleotide to the 3'-terminal of a nucleic acid, and a labeling compound binding step of either binding a labeling compound having a lysine (Lys) residue and containing a labeling moiety to the glutamine (Gln) residue using a transglutaminase (TGase), or binding a labeling compound having a glutamine (Gln) residue and containing a labeling moiety to the lysine (Lys) residue using a transglutaminase (TGase).

12 Claims, 19 Drawing Sheets

Z-QG
NHS-modified Z-QG
Aminoallyl-dUTP
Z-QG-dUTP

(51) Int. Cl.

| | |
|---|---|
| ***G01N 33/53*** | (2006.01) |
| ***G01N 33/532*** | (2006.01) |
| ***G01N 33/58*** | (2006.01) |
| ***C12P 21/02*** | (2006.01) |

(56) References Cited

U.S. PATENT DOCUMENTS

| | | | |
|---|---|---|---|
| 6,340,747 | B1 | 1/2002 | Bazin et al. |
| 2011/0189671 | A1 | 8/2011 | Kamiya et al. |

FOREIGN PATENT DOCUMENTS

| | | | | |
|---|---|---|---|---|
| JP | 2002-507203 | A | | 3/2002 |
| JP | 2008-54658 | A | | 3/2008 |
| JP | 2011-169878 | A | | 9/2011 |
| WO | WO 01/19841 | | * | 3/2001 |
| WO | 2010/010966 | A1 | | 1/2010 |

OTHER PUBLICATIONS

Baldrich et al., "Aptasensor Development: Elucidation of Critical Parameters for Optimal Aptamer Performance" Analytical Chemistry, vol. 76, No. 23, Dec. 1, 2004, pp. 7053-7063.

Kuwahara et al., "Direct PCR amplification of various modified DNAs having amino acids: Convenient preparation of DNA libraries with high-potential activities for in vitro selection", Bioorganic & Medicinal Chemistry, vol. 14(8), 2006, pp. 2518-2526.

Notice of Grounds for Rejection dated Sep. 10, 2013 issued in corresponding application JP2012-141089, 6 pages; English translation.

International Search Report dated Sep. 17, 2013 issued in corresponding application No. PCT/JP2013/067018.

Extended European Search Report dated Feb. 5, 2016, issued in counterpart European Patent Application No. 13807729.2. (10 pages).

Momoko Kitaoka et al., "Transglutaminase-Mediated Synthesis of a DNA-(Enzyme)n, Probe for Highly Sensitive DNA Detection," Chemistry—A European Journal., vol. 17, No. 19, Apr. 5, 2011, pp. 5387-5392.

Momoko Kitaoka et al., "Transglutaminase-Mediated in Situ Hybridization (TransISH) System: A New Methodology for Simplified mRNA Detection," Analytical Chemistry, vol. 84, No. 14, Jun. 10, 2012, pp. 5885-5891.

Mari Takahara et al., "Tailing DNA Aptamers with a Functional Protein by Two-Step Enzymatic Reaction," Journal of Bioscience and Bioengineering, vol. 116, No. 6, Dec. 1, 2013, pp. 660-665.

Cesar Guerra, "Analysis of oligonucleotide Microarrays by 3' end Labeling using Fluorescent Nucleotides and Terminal Transferase," Biotechniques, vol. 41, No. 1, Jul. 1, 2006, pp. 53-56.

Notification of transmittal of translation of the International Preliminary Report on Patentability (Chapter I or Chapter II) (Form PCT/IB/338) of the International Application No. PCT/JP2013/067018 mailed Dec. 24, 2014, with form PCT/IPEA/409. (6 pages).

International Preliminary Report on Patentability (Chapter I) International application No. PCT/JP2013/067018 mailed Sep. 17, 2013, (PCT/ISA/237) w/Partial translation. (7 pages).

* cited by examiner (a) $(Z\text{-}QG)_m$ -DNA (b) (Z-QG)-DNA

M: 100bp DNA ladder (NEB)

1: Before reaction

2: After reaction

M : 1kbp DNA ladder (NEB)

1: Before $(PfuAP)_n$-DNA reaction

2: After $(PfuAP)_n$-DNA reaction

3: Before (PfuAP)-DNA reaction

4: After (PfuAP)-DNA reaction

Lane conditions
1: TemplateDNA
2: 5min
3: 10min
4: 20min
5: 30min
6: 60min

Lane conditions
1: TemplateDNA
2: Z-QG-dUTP (100%)
3: Z-QG-dUTP (25%)+dATP (75%)
4: Z-QG-dUTP (25%)+dTTP (75%)
5: Z-QG-dUTP (25%)+dCTP (75%)
6: Z-QG-dUTP (25%)+dGTP (75%)

Change in concentrations of Z-QG-dUTP and dTTP

Lane conditions

1: TemplateDNA
2: Z-QG-dUTP (100%)
3: Z-QG-dUTP (75%)+dTTP (25%)
4: Z-QG-dUTP (50%)+dTTP (50%)
5: Z-QG-dUTP (25%)+dTTP (75%)
6: dTTP (100%)

Change in concentrations of Z-QG-dUTP and dATP

Lane conditions

1: TemplateDNA
2: Z-QG-dUTP (100%)
3: Z-QG-dUTP (75%)+dATP (25%)
4: Z-QG-dUTP (50%)+dATP (50%)
5: Z-QG-dUTP (25%)+dATP (75%)
6: dATP (100%)

CHROMATOGRAM 1 MEMORIZED

C-R5A CHROMATOPAC
CHANNEL NO 1 FILE 0
SAMPLE NO 0 METHOD 41
REPORT NO 2672

| PKNO | TIME | AREA | MK | IDNO | CONC | NAME |
|---|---|---|---|---|---|---|
| 1 | 1.554 | 867 | | | 0.1973 | |
| 2 | 1.763 | 828 | | | 0.1884 | |
| 3 | 11.451 | 437598 | | | 99.6143 | |
| | TOTAL | 439292 | | | 100 | |

CHROMATOGRAM 1 MEMORIZED

C-R5A CHROMATOPAC
CHANNEL NO 1 FILE 0
SAMPLE NO 0 METHOD 41
REPORT NO 2749

| PKNO | TIME | AREA | MK | IDNO | CONC | NAME |
|---|---|---|---|---|---|---|
| 1 | 15.297 | 7233 | | | 1.6847 | |
| 2 | 16.382 | 422082 | V | | 98.3153 | |
| | TOTAL | 429314 | | | 100 | |

(a) (b)

SEQUENCE LISTING

```
<160> NUMBER OF SEQ ID NOS: 31

<210> SEQ ID NO 1
<211> LENGTH: 4
<212> TYPE: PRT
```

-continued

<213> ORGANISM: Artificial Sequence
<220> FEATURE:
<223> OTHER INFORMATION: Chemically synthesized

<400> SEQUENCE: 1

Leu Leu Gln Gly
1

<210> SEQ ID NO 2
<211> LENGTH: 4
<212> TYPE: PRT
<213> ORGANISM: Artificial Sequence
<220> FEATURE:
<223> OTHER INFORMATION: Chemically synthesized

<400> SEQUENCE: 2

Leu Ala Gln Gly
1

<210> SEQ ID NO 3
<211> LENGTH: 4
<212> TYPE: PRT
<213> ORGANISM: Artificial Sequence
<220> FEATURE:
<223> OTHER INFORMATION: Chemically synthesized

<400> SEQUENCE: 3

Leu Gly Gln Gly
1

<210> SEQ ID NO 4
<211> LENGTH: 6
<212> TYPE: PRT
<213> ORGANISM: Artificial Sequence
<220> FEATURE:
<223> OTHER INFORMATION: Chemically synthesized

<400> SEQUENCE: 4

Pro Leu Ala Gln Ser His
1               5

<210> SEQ ID NO 5
<211> LENGTH: 8
<212> TYPE: PRT
<213> ORGANISM: Artificial Sequence
<220> FEATURE:
<223> OTHER INFORMATION: Chemically synthesized

<400> SEQUENCE: 5

Phe Glu Arg Gln His Met Asp Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Chemically synthesized

<400> SEQUENCE: 6

Thr Glu Gln Lys Leu Ile Ser Glu Glu Asp Leu
1               5                   10

<210> SEQ ID NO 7
<211> LENGTH: 7
<212> TYPE: PRT
<213> ORGANISM: Artificial Sequence -continued
<220> FEATURE:
<223> OTHER INFORMATION: Chemically synthesized

<400> SEQUENCE: 7

Gly Leu Gly Gln Gly Gly Gly
1 5

<210> SEQ ID NO 8
<211> LENGTH: 7
<212> TYPE: PRT
<213> ORGANISM: Artificial Sequence
<220> FEATURE:
<223> OTHER INFORMATION: Chemically synthesized

<400> SEQUENCE: 8

Gly Phe Gly Gln Gly Gly Gly
1 5

<210> SEQ ID NO 9
<211> LENGTH: 7
<212> TYPE: PRT
<213> ORGANISM: Artificial Sequence
<220> FEATURE:
<223> OTHER INFORMATION: Chemically synthesized

<400> SEQUENCE: 9

Gly Val Gly Gln Gly Gly Gly
1 5

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized

<400> SEQUENCE: 10

Gly Gly Leu Gln Gly Gly Gly
1 5

<210> SEQ ID NO 11
<211> LENGTH: 7
<212> TYPE: PRT
<213> ORGANISM: Artificial Sequence
<220> FEATURE:
<223> OTHER INFORMATION: Chemically synthesized

<400> SEQUENCE: 11

Glu Ala Gln Gln Ile Val Met
1 5

<210> SEQ ID NO 12
<211> LENGTH: 7
<212> TYPE: PRT
<213> ORGANISM: Artificial Sequence
<220> FEATURE:
<223> OTHER INFORMATION: Chemically synthesized

<400> SEQUENCE: 12

Gly Gly Gly Gln Leu Gly Gly
1 5

<210> SEQ ID NO 13
<211> LENGTH: 7
<212> TYPE: PRT
<213> ORGANISM: Artificial Sequence
<220> FEATURE:

<223> OTHER INFORMATION: Chemically synthesized

<400> SEQUENCE: 13

Gly Gly Gly Gln Val Gly Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Chemically synthesized

<400> SEQUENCE: 14

Gly Gly Gly Gln Arg Gly Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Chemically synthesized

<400> SEQUENCE: 15

Gly Gln Gln Gln Leu Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Chemically synthesized

<400> SEQUENCE: 16

Pro Asn Pro Gln Leu Pro Phe
1               5

<210> SEQ ID NO 17
<211> LENGTH: 7
<212> TYPE: PRT
<213> ORGANISM: Artificial Sequence
<220> FEATURE:
<223> OTHER INFORMATION: Chemically synthesized

<400> SEQUENCE: 17

Pro Lys Pro Gln Gln Phe Met
1               5

<210> SEQ ID NO 18
<211> LENGTH: 6
<212> TYPE: PRT
<213> ORGANISM: Artificial Sequence
<220> FEATURE:
<223> OTHER INFORMATION: Chemically synthesized

<400> SEQUENCE: 18

Met Lys His Lys Gly Ser
1               5

<210> SEQ ID NO 19
<211> LENGTH: 21
<212> TYPE: PRT
<213> ORGANISM: Artificial Sequence
<220> FEATURE:
<223> OTHER INFORMATION: Chemically synthesized

<400> SEQUENCE: 19

Gly Ser Gly Met Lys Glu Thr Ala Ala Ala Arg Phe Glu Arg Ala His
1 5 10 15

Met Asp Ser Gly Ser
20

<210> SEQ ID NO 20
<211> LENGTH: 13
<212> TYPE: PRT
<213> ORGANISM: Artificial Sequence
<220> FEATURE:
<223> OTHER INFORMATION: Chemically synthesized

<400> SEQUENCE: 20

Met Gly Gly Ser Thr Lys His Lys Ile Pro Gly Gly Ser
1 5 10

<210> SEQ ID NO 21
<211> LENGTH: 5
<212> TYPE: PRT
<213> ORGANISM: Artificial Sequence
<220> FEATURE:
<223> OTHER INFORMATION: Chemically synthesized

<400> SEQUENCE: 21

Gly Gly Gly Gly Gly
1 5

<210> SEQ ID NO 22
<211> LENGTH: 14
<212> TYPE: PRT
<213> ORGANISM: Artificial Sequence
<220> FEATURE:
<223> OTHER INFORMATION: Chemically synthesized

<400> SEQUENCE: 22

Met Lys His Lys Gly Ser Gly Gly Gly Ser Gly Gly Gly Ser
1 5 10

<210> SEQ ID NO 23
<211> LENGTH: 6
<212> TYPE: PRT
<213> ORGANISM: Artificial Sequence
<220> FEATURE:
<223> OTHER INFORMATION: Chemically synthesized

<400> SEQUENCE: 23

Met Arg His Lys Gly Ser
1 5

<210> SEQ ID NO 24
<211> LENGTH: 6
<212> TYPE: PRT
<213> ORGANISM: Artificial Sequence
<220> FEATURE:
<223> OTHER INFORMATION: Chemically synthesized

<400> SEQUENCE: 24

Met Arg Arg Lys Gly Ser
1 5

<210> SEQ ID NO 25
<211> LENGTH: 6
<212> TYPE: PRT
<213> ORGANISM: Artificial Sequence -continued
<220> FEATURE:
<223> OTHER INFORMATION: Chemically synthesized

<400> SEQUENCE: 25

Met His Arg Lys Gly Ser
1 5

<210> SEQ ID NO 26
<211> LENGTH: 3685
<212> TYPE: DNA
<213> ORGANISM: Artificial Sequence
<220> FEATURE:
<223> OTHER INFORMATION: Chemically synthesized

<400> SEQUENCE: 26
acgtgccgat caacgtctca ttttcgccaa aagttggccc agggcttccc ggtatcaaca 60
gggacaccag gatttattta ttctgcgaag tgatcttccg ttcgacggag ttccactgag 120
cgtcagaccc cgtagaaaag atcaaaggat cttcttgaga tccttttttt ctgcgcgtaa 180
tctgctgctt gcaaacaaaa aaaccaccgc taccagcggt ggtttgtttg ccggatcaag 240
agctaccaac tctttttccg aaggtaactg gcttcagcag agcgcagata ccaaatactg 300
tccttctagt gtagccgtag ttaggccacc acttcaagaa ctctgtagca ccgcctacat 360
acctcgctct gctaatcctg ttaccagtgg ctgctgccag tggcgataag tcgtgtctta 420
ccgggttgga ctcaagacga tagttaccgg ataaggcgca gcggtcgggc tgaacggggg 480
gttcgtgcac acagcccagc ttggagcgaa cgacctacac cgaactgaga tacctacagc 540
gtgagcattg agaaagcgcc acgcttcccg aagggagaaa ggcggacagg tatccggtaa 600
gcggcagggt cggaacagga gagcgcacga gggagcttcc agggggaaac gcctggtatc 660
tttatagtcc tgtcgggttt cgccacctct gacttgagcg tcgatttttg tgatgctcgt 720
caggggggcg gagcctatgg aaaaacgcca gcaacgcggc ctttttacgg ttcctggcct 780
tttgctggcc ttttgctcac atgttctttc ctgcgttatc ccctgattct gtggataacc 840
gtattaccgc ctttgagtga gctgataccg ctcgccgcag ccgaacgacc gagcgcagcg 900
agtcagtgag cgaggaagcg gaagaagctc attcgccatt caggctgcgc aactgttggg 960
aagggcgatc ggtgcgggcc tcttcgctat tacgccagct ggcgaaaggg ggatgtgctg 1020
caaggcgatt aagttgggta acgccagggt tttcccagtc acgacgttgt aaaacgacgg 1080
ccagtgaatt ccatatgaaa cataaaggcg gaggttcagg tggcggatct ggcagtgctt 1140
acgattctca ggaaagtggg attaaaaata tcattatcct gattggcgac ggtatgggga 1200
tgtcgcacgt gcaaatcacc aaactggttt acggccatct gaacatggag gagttcccta 1260
ttatcgggtt tgagctgact gaaagcctgt cgggcgaagt caccgatagt gccgcagctg 1320
gtacagcgat tgccaccggg gtaaagacgt ataaccgtat gatttctgtc acgaatatta 1380
caggcaaagt taccaatctg accacgctgc tggagatcgc acaggtcctg ggtaaatcca 1440
ctgggctggt aacaacgacc cgcattactc acgcgacgcc ggcagtattt gcctcgcacg 1500
ttccggaccg tgatatggaa gaggaaatcg cacgccaact gattgctcac cgtgttaacg 1560
tactgctggg tgggggacgc aagaagttcg acgaaaatac cctgaaaatg gctaaggagc 1620
aagggtacaa tatcgtattt actaaagagg aactggaaaa agccgaaggg gagtttatcc 1680
tgggactgtt cgcagacagt cacattccgt acgttctgga ccgtaagccg gaggacgtcg 1740
gactgctgga gatgaccaaa aaagctatct ctattctgga aaagaatccg aacggttttt 1800
tcctgatgat cgaaggtggg cgtattgatc acgcggccca cgagaacgat atcgcaagtg 1860

```
tcgttgcgga aactaaagag ttcgatgacg tagtgggcta cgtcctggag tatgctaaaa   1920

agcgtggtga tacactggtt attgtcctgg ctgatcacga aacgggggc ctgggtctgg   1980

gcctgacata cggtgacgca atcaacgagg atgtaattcg caatatcaat gcgtcggtat   2040

ccaagatcgc gagcgagatt cgcgccacca acgatattaa acgcgttatt aagaaatata   2100

cagggtttga actgacggag gatgaaatta actatatcga agaggcgatt aacctggcgg   2160

atgaatacgc gctgcaaaac gctattgcag atattattaa taaacgtgtg ggcgtaggtt   2220

ttgtatccca caagcacacg ggggcgccag tctctctgct ggcttatggt ccgggggcag   2280

agaacttcgc gggctttctg caccacgtcg atactgctaa actgatcgcc aaactgatgc   2340

tgttcggtaa gaaagatatt ccggtcacaa ttctgggtat ttctggagtt aaaggtgata   2400

tcaccggcga ctttaaggta gatgaacaag atgcgtacgt cacactgatg atgctgctgg   2460

gtgagcgcgt cgatacggaa ctggaacgta aagtggatat gaataacaat ggaattattg   2520

aactggggga cgtactgctg atcctgcaag agtcgggttc ccaccaccac caccaccact   2580

aaggatccga attcaagctt ggcgtaatca tggtcatagc tgtttcctgt gtgaaattgt   2640

tatccgctca caattccaca caacatacga gccggaagca taaagtgtaa agcctggggt   2700

gcctaatgag tgagctaact cacattaatt gcgttgcgct cactgcccgc tttccagtcg   2760

ggaaacctgt cgtgccagct gcattaatga atcggccaac gcgcggggag aggcggtttg   2820

cgtattggag cttggcactg gccaagctg aatttctgcc attcatccgc ttattatcac   2880

ttattcaggc gtagcaccag gcgtttaagg gcaccaataa ctgccttaaa aaaattacgc   2940

cccgccctgc cactcatcgc agtactgttg taattcatta agcattctgc cgacatggaa   3000

gccatcacag acggcatgat gaacctgaat cgccagcggc atcagcacct tgtcgccttg   3060

cgtataatat ttgcccatgg tgaaaacggg ggcgaagaag ttgtccatat tggccacgtt   3120

taaatcaaaa ctggtgaaac tcacccaggg attggctgag acgaaaaaca tattctcaat   3180

aaaccccttta gggaaatagg ccaggttttc accgtaacac gccacatctt gcgaatatat   3240

gtgtagaaac tgccggaaat cgtcgtggta ttcactccag agcgatgaaa acgtttcagt   3300

ttgctcatgg aaaacggtgt aacaagggtg aacactatcc catatcacca gctcaccgtc   3360

tttcattgcc atacgaaatt ccggatgagc attcatcagg cgggcaagaa tgtgaataaa   3420

ggccggataa aacttgtgct tatttttctt tacggtcttt aaaaaggccg taatatccag   3480

ctgaacggtc tggttatagg tacattgagc aactgactga aatgcctcaa aatgttcttt   3540

acgatgccat tgggatatat caacggtggt atatccagtg atttttttct ccattttagc   3600

ttccttagct cctgaaaatc tcgataactc aaaaaatacg cccggtagtg atcttatttc   3660

attatggtga aagttggaac ctctt                                         3685
```

<210> SEQ ID NO 27
<211> LENGTH: 301
<212> TYPE: DNA
<213> ORGANISM: Artificial Sequence
<220> FEATURE:
<223> OTHER INFORMATION: Chemically synthesized

<400> SEQUENCE: 27

```
aggaaaacac gggagcagac cggctgatga ctcagaggtg caaagacaag ttaaatgcct     60

tggccatctc tgtgatgaac cagtggcctg gagtgaagct gcgagtgacc gagggctggg    120

atgaggacgg ccatcattca gaggagtctc tacactatga ggggtcgagc agtggacatc    180
```

-continued accacgtccg accgggaccg cagcaagtac ggcatgctgg ctcgcctggc tgtggaagca 240
ggtttcgact gggtctacta tgaatccaaa gctcacatcc actgttctgt gaaagcagag 300
a 301

<210> SEQ ID NO 28
<211> LENGTH: 956
<212> TYPE: DNA
<213> ORGANISM: Artificial Sequence
<220> FEATURE:
<223> OTHER INFORMATION: Chemically synthesized

<400> SEQUENCE: 28
aattaaccct cactaaaggg cgcagcacag agtatggtgt gggctactcc tgtgacgcgg 60
gtctgcacgg ctggtaccgg ttcacaggcc agggtggcgt tcgcatggct gagacctgtg 120
tgcccgtcct gcgatgcaac acggcggcac ccatgtggct caatggctct catccctcga 180
gtagtgaagg cattgtgagc cgcacggcct gtgcacactg gagcgaccaa tgctgccggt 240
ggtccacaga gatccaggtg aaggcttgcc caggtggctt ctatatttac aacttgacag 300
cgccccctga gtgcaatctg gcttactgca ccgatcctag ttccgtggag ggacttgcg 360 aagaatgcag ggtagatgaa gattgcatat cggataacgg cagatggcgc tgccagtgta 420
aacaggactc caacatcaca gatgtctccc aattggagta caggctggag tgtggggcca 480
atgacatcaa gatgtccctc agaaagtgcc agctacagag tttgggcttt atgaatgtct 540
tcatgtacct gaatgacaga caatgctcag gcttcagtga gagtgatgaa cgagactgga 600
tgtccatagt gacccctgcc aggaatggtc cctgtgggac agtattgagg agaaacgaaa 660
cccatgccac ctacagcaac accctctacc tggcaaatgc gatcatcatt cgggacatca 720
tcataagaat gaactttgaa tgctcttacc ctctggacat gaaagtcagc ctgaagacct 780
ccctacagcc catggtcagt gccctgaaca tcagcttggg tgggacaggc aagttcaccg 840
tgcggatggc attgttccag agccctacct acacacagcc ccaccaaggt ccttctgtga 900
tgctgtccac tgaggctttt ctgtatgtgg gcaccaccct atagtgagtc gtatta 956

<210> SEQ ID NO 29
<211> LENGTH: 30
<212> TYPE: DNA
<213> ORGANISM: Artificial Sequence
<220> FEATURE:
<223> OTHER INFORMATION: Chemically synthesized

<400> SEQUENCE: 29
ggttggtgtg gttggttttt tttttttttt 30

<210> SEQ ID NO 30
<211> LENGTH: 473
<212> TYPE: PRT
<213> ORGANISM: Artificial Sequence
<220> FEATURE:
<223> OTHER INFORMATION: Chemically synthesized

<400> SEQUENCE: 30

Met Lys His Lys Gly Gly Gly Ser Gly Gly Gly Ser Gly Ser Thr Pro
1 5 10 15

Ser Met Pro Val Leu Glu Asn Arg Ala Ala Gln Gly Asp Ile Thr Ala
20 25 30

Pro Gly Gly Ala Arg Arg Leu Thr Gly Asp Gln Thr Ala Ala Leu Arg
35 40 45

-continued

```
Asp Ser Leu Ser Asp Lys Pro Ala Lys Asn Ile Ile Leu Leu Ile Gly
    50                  55                  60

Asp Gly Met Gly Asp Ser Glu Ile Thr Ala Ala Arg Asn Tyr Ala Glu
65                  70                  75                  80

Gly Ala Gly Gly Phe Phe Lys Gly Ile Asp Ala Leu Pro Leu Thr Gly
                85                  90                  95

Gln Tyr Thr His Tyr Ala Leu Asn Lys Lys Thr Gly Lys Pro Asp Tyr
            100                 105                 110

Val Thr Asp Ser Ala Ala Ser Ala Thr Ala Trp Ser Thr Gly Val Lys
        115                 120                 125

Thr Tyr Asn Gly Ala Leu Gly Val Asp Ile His Glu Lys Asp His Pro
    130                 135                 140

Thr Ile Leu Glu Met Ala Lys Ala Ala Gly Leu Ala Thr Gly Asn Val
145                 150                 155                 160

Ser Thr Ala Glu Leu Gln Asp Ala Thr Pro Ala Ala Leu Val Ala His
                165                 170                 175

Val Thr Ser Arg Lys Cys Tyr Gly Pro Ser Ala Thr Ser Glu Lys Cys
            180                 185                 190

Pro Gly Asn Ala Leu Glu Lys Gly Gly Lys Gly Ser Ile Thr Glu Gln
        195                 200                 205

Leu Leu Asn Ala Arg Ala Asp Val Thr Leu Gly Gly Gly Ala Lys Thr
    210                 215                 220

Phe Ala Glu Thr Ala Thr Ala Gly Glu Trp Gln Gly Lys Thr Leu Arg
225                 230                 235                 240

Glu Gln Ala Gln Ala Arg Gly Tyr Gln Leu Val Ser Asp Ala Ala Ser
                245                 250                 255

Leu Asn Ser Val Thr Glu Ala Asn Gln Gln Lys Pro Leu Leu Gly Leu
            260                 265                 270

Phe Ala Asp Gly Asn Met Pro Val Arg Trp Leu Gly Pro Lys Ala Thr
        275                 280                 285

Tyr His Gly Asn Ile Asp Lys Pro Ala Val Thr Cys Thr Pro Asn Pro
    290                 295                 300

Gln Arg Asn Asp Ser Val Pro Thr Leu Ala Gln Met Thr Asp Lys Ala
305                 310                 315                 320

Ile Glu Leu Leu Ser Lys Asn Glu Lys Gly Phe Phe Leu Gln Val Glu
                325                 330                 335

Gly Ala Ser Ile Asp Lys Gln Asp His Ala Ala Asn Pro Cys Gly Gln
            340                 345                 350

Ile Gly Glu Thr Val Asp Leu Asp Glu Ala Val Gln Arg Ala Leu Glu
        355                 360                 365

Phe Ala Lys Lys Glu Gly Asn Thr Leu Val Ile Val Thr Ala Asp His
    370                 375                 380

Ala His Ala Ser Gln Ile Val Ala Pro Asp Thr Lys Ala Pro Gly Leu
385                 390                 395                 400

Thr Gln Ala Leu Asn Thr Lys Asp Gly Ala Val Met Val Met Ser Tyr
                405                 410                 415

Gly Asn Ser Glu Glu Asp Ser Gln Glu His Thr Gly Ser Gln Leu Arg
            420                 425                 430

Ile Ala Ala Tyr Gly Pro His Ala Ala Asn Val Val Gly Leu Thr Asp
        435                 440                 445

Gln Thr Asp Leu Phe Tyr Thr Met Lys Ala Ala Leu Gly Leu Lys Met
    450                 455                 460
```

Lys His Lys His His His His His His
465 470

<210> SEQ ID NO 31
<211> LENGTH: 1479
<212> TYPE: DNA
<213> ORGANISM: Artificial Sequence
<220> FEATURE:
<223> OTHER INFORMATION: Chemically synthesized

<400> SEQUENCE: 31
atgaaatacc tgctgccgac cgctgctgct ggtctgctgc tcctcgctgc ccagccggcg 60
atggccatga aacataaagg aggtggttcc ggtggtggtt ccggatccac cccatccatg 120
cctgttctag aaaaccgggc tgctcagggc gatattactg cacccggcgg tgctcgccgt 180
ttaacgggtg atcagactgc cgctctgcgt gattctctta gcgataaacc tgcaaaaaat 240
attattttgc tgattggcga tgggatgggg gactcggaaa ttactgccgc acgtaattat 300
gccgaaggtg cgggcggctt ttttaaaggt atagatgcct taccgcttac cgggcaatac 360
actcactatg cgctgaataa aaaaaccggc aaaccggact acgtcaccga ctcggctgca 420
tcagcaaccg cctggtcaac cggtgtcaaa acctataacg gcgcgctggg cgtcgatatt 480
cacgaaaaag atcacccaac gattctggaa atggcaaaag ccgcaggtct ggcgaccggt 540
aacgtttcta ccgcagagtt gcaggatgcc acgcccgctg cgctggtggc acatgtgacc 600
tcgcgcaaat gctacggtcc gagcgcgacc agtgaaaaat gtccgggtaa cgctctggaa 660
aaaggcggaa aaggatcgat taccgaacag ctgcttaacg ctcgtgccga cgttacgctt 720
ggcggcggcg caaaaacctt tgctgaaacg gcaaccgctg gtgaatggca gggaaaaacg 780
ctgcgtgaac aggcacaggc gcgtggttat cagttggtga gcgatgctgc ctcactgaat 840
tcggtgacgg aagcgaatca gcaaaaaccc ctgcttggcc tgtttgctga cggcaatatg 900
ccagtgcgct ggctaggacc gaaagcaacg taccatggca atatcgataa gcccgcagtc 960
acctgtacgc caaatccgca acgtaatgac agtgtaccaa ccctggcgca gatgaccgac 1020
aaagccattg aattgttgag taaaaatgag aaaggctttt tcctgcaagt tgaaggtgcg 1080
tcaatcgata aacaggatca tgctgcgaat ccttgtgggc aaattggcga gacggtcgat 1140
ctcgatgaag ccgtacaacg ggcgctggaa ttcgctaaaa aggagggtaa cacgctggtc 1200
atagtcaccg ctgatcacgc ccacgccagc cagattgttg cgccggatac caaagctccg 1260
ggcctcaccc aggcgctaaa taccaaagat ggcgcagtga tggtgatgag ttacgggaac 1320
tccgaagagg attcacaaga acataccggc agtcagttgc gtattgcggc gtatggcccg 1380
catgccgcca atgttgttgg actgaccgac cagaccgatc tcttctacac catgaaagcc 1440
gctctggggc tgaaactcga gcaccaccac caccaccac 1479

METHOD FOR PRODUCING PROTEIN-NUCLEIC ACID CONJUGATE, AND METHOD FOR DETECTING TARGET SUBSTANCE

TECHNICAL FIELD

The present invention relates to a method for producing a protein-nucleic acid conjugate and a method for detecting a target substance.

BACKGROUND ART

By using a nucleic acid probe such as an RNA probe or DNA probe that has been subjected to some form of labeling to detect and visualize the expression pattern of DNA or RNA at a cellular level, a multitude of problems related to vital phenomena can be explained. The labeling methods employed for the probes used in these cases can be broadly classified into "radioactive isotope labeling methods", "fluorescent labeling methods" and "enzyme labeling methods." Historically, nucleic acid probes having an introduced radioactive isotope were developed first, but in recent years, restrictions have been introduced relating to the handling of such probes, and therefore fluorescent labeling methods and enzyme labeling methods, which do not require the use of a radioactive isotope element, are attracting much attention.

In recent years, aptamers having binding specificity to organic small molecules or biopolymers such as proteins are attracting attention as detection ligands. Nucleic acid aptamers are oligonucleotides (DNA or RNA) that able to bind wide variety of target substances with high affinity and specificity by their higher order structure.

A chemical binding method is usually used as the method for introducing a labeling moiety such as an enzyme into a nucleic acid such as a nucleic acid aptamer. However, the chemical reaction may sometimes cause a deterioration in the target substance recognition ability of the nucleic acid aptamer or the like, or a deterioration in the performance of the labeling moiety. Particularly in those cases where the labeling moiety is an enzyme, the performance of the enzyme is prone to deterioration. Accordingly, there is much demand for a method for modifying a nucleic acid such as a nucleic acid aptamer while maintaining both the recognition ability of the nucleic acid aptamer or the like and the function of the labeling moiety. In other words, in order to maintain the functions of both the nucleic acid aptamer or the like and the labeling moiety, a modification method that strongly suppresses any effects on the target substance recognition site of the nucleic acid aptamer or the like, and on other active sites such as the labeling enzyme, namely a site-specific modification method, is very desirable.

On the other hand, a method is known in which a transglutaminase (TGase) is used to achieve site-specific binding of an exogenous molecule which is anionic and has a glutamine (Gln) residue that is recognizable by TGase to a peptide or protein having a lysine (Lys) residue or a primary amine that are recognizable by TGase (for example, see Patent Document 1).

PRIOR ART

Patent Document

PATENT DOCUMENT 1: JP 2008-054658 A

DISCLOSURE OF INVENTION

Problems to be Solved by the Invention

Objects of the present invention are to provide a method for producing a protein-nucleic acid conjugate that can detect a target substance with good sensitivity, and to provide a method for detecting a target substance.

Means for Solving the Problems

The present invention provides a method for producing a protein-nucleic acid conjugate, the method comprising a 3'-terminal addition step of adding at least one nucleoside triphosphate derivative having a glutamine (Gln) residue or a lysine (Lys) residue to the 3'-terminal of a nucleic acid using a 3'-terminal addition enzyme which adds a nucleotide to the 3'-terminal of a nucleic acid, and a labeling compound binding step of either binding a labeling compound having a lysine (Lys) residue and containing a labeling moiety to the above-mentioned glutamine (Gln) residue using a transglutaminase (TGase), or binding a labeling compound having a glutamine (Gin) residue and containing a labeling moiety to the above-mentioned lysine (Lys) residue using a transglutaminase (TGase).

Further, in the method for producing a protein-nucleic acid conjugate described above, the 3'-terminal addition enzyme is preferably at least one of terminal deoxynucleotidyl transferase (TdT), Family A-type DNA polymerase, and poly(A) RNA polymerase.

Furthermore, in the method for producing a protein-nucleic acid conjugate described above, the nucleoside triphosphate derivative is preferably represented by formula (1) shown below.

(1)

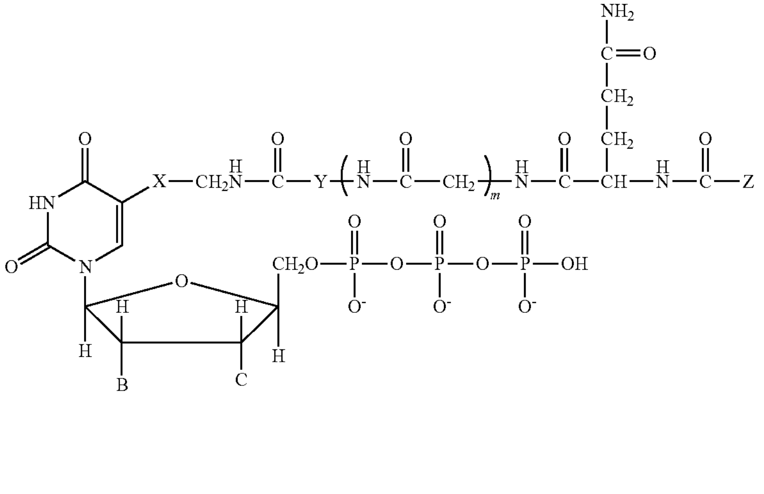

In formula (1), each of X and Y independently represents an alkylene group having a carbon number of 1 to 48 or an alkenylene group having a carbon number of 2 to 48 which may be substituted with an ethenylene group, $-(C_2H_4O)_n-$ group or $-(C_3H_6O)_n-$ group (wherein n=2, 4, 8, 12 or 24), and Z represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48, which may be substituted with a dinitrophenyl group or an L-3,4-dihydroxyphenyl group. Further, at least one of Y and Z may be independently substituted with an amino acid other than Lys. B represents a hydrogen atom or a hydroxyl group, C represents a hydrogen atom or a hydroxyl group, and m represents 0 or 1.

Further, in the method for producing a protein-nucleic acid conjugate described above, it is preferable that X represents an ethenylene group, Y represents a methylene group, and Z represents a benzyloxy group.

Furthermore, the present invention also provides a method for detecting a target substance, the method comprising binding, via nucleic acid moieties, a protein-nucleic acid conjugate, which is obtained by a method for producing a protein-nucleic acid conjugate comprising a 3'-terminal addition step of adding at least one nucleoside triphosphate derivative having a glutamine (Gln) residue or a lysine (Lys) residue to the 3'-terminal of a nucleic acid using a 3'-terminal addition enzyme which adds a nucleotide to the 3'-terminal of a nucleic acid, and a labeling compound binding step of either binding a labeling compound having a lysine (Lys) residue and containing a labeling moiety to the above-mentioned glutamine (Gln) residue using a transglutaminase (TGase), or binding a labeling compound having a glutamine (Gln) residue and containing a labeling moiety to the above-mentioned lysine (Lys) residue using a transglutaminase (TGase), and a target substance which exists within a target material, and detecting the bound protein-nucleic acid conjugate by the labeling moiety.

Advantages of the Invention

In the present invention, by adding at least one nucleoside triphosphate derivative having a glutamine (Gln) residue or the like to the 3'-terminal of a nucleic acid using a 3'-terminal addition enzyme, and subsequently binding a labeling compound having a lysine (Lys) residue or the like and containing a labeling moiety to the glutamine (Gln) residue or the like using a transglutaminase (TGase), the invention is able to provide a method for producing a protein-nucleic acid conjugate that can detect a target substance with good sensitivity.

Further, in the present invention, by using the protein-nucleic acid conjugate, a method for detecting a target substance which enables the target substance to be detected with good sensitivity can be provided.

EMBODIMENTS FOR CARRYING OUT THE INVENTION

Figure 1:
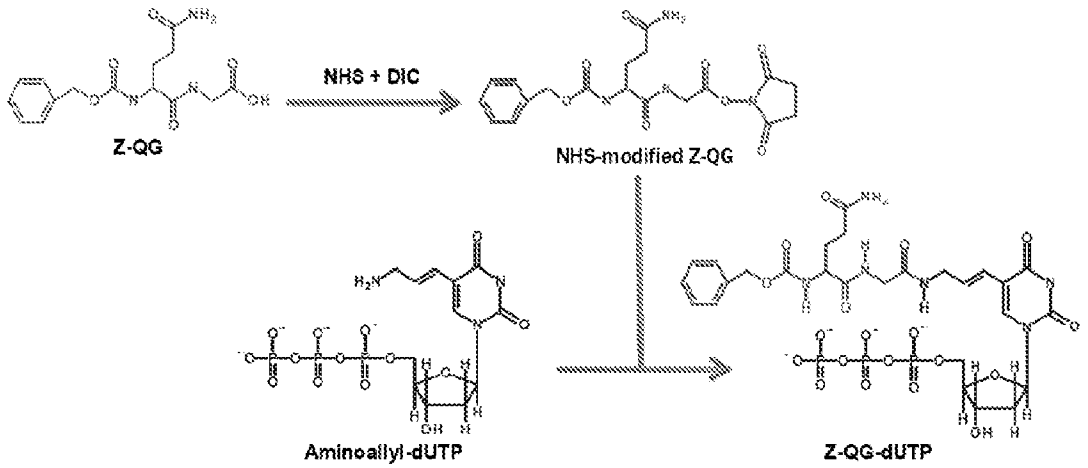
FIG. 1 is a diagram illustrating one example of a method for synthesizing Z-QG-dUTP, which represents one example of a nucleotide derivative according to an embodiment of the present invention.

Embodiments of the present invention are described below. These embodiments are merely examples of implementing the present invention, and the present invention is in no way limited by these embodiments.

A method for producing a protein-nucleic acid conjugate according to an embodiment of the present invention comprises a 3'-terminal addition step of adding at least one nucleoside triphosphate derivative having a glutamine (Gln) residue or a lysine (Lys) residue to the 3'-terminal of a nucleic acid using a 3'-terminal addition enzyme which adds a nucleotide to the 3'-terminal of a nucleic acid, and a labeling compound binding step of either binding a labeling compound having a lysine (Lys) residue and containing a labeling moiety to the above-mentioned glutamine (Gln) residue using a transglutaminase (TGase), or binding a labeling compound having a glutamine (Gln) residue and containing a labeling moiety to the above-mentioned lysine (Lys) residue using a transglutaminase (TGase).

The inventors of the present invention focused their attention on a site-specific modification method using a 3'-terminal addition enzyme such as TdT as a technique for adding a nucleotide to the 3'-terminal of a nucleic acid in order to maintain the higher order structure formation sequence of the nucleic acid. These 3'-terminal addition enzymes such as TdT are enzymes which randomly add a deoxynucleotide to the 3'-terminal of a nucleic acid, and can produce a homopolymer in a non-template dependent manner. TdT and the like are considered to have poor substrate recognition, and to be capable of incorporating chemically modified nucleotides. As a result, by incorporating a nucleotide in which a reactive site has been modified for introducing a labeling compound, TdT or the like can be used for nucleic acid extension and reactive site introduction. Further, TdT and the like produce a homopolymer at the 3'-terminal in a non-template dependent manner, meaning there is almost no effect on the higher order structure formation sequence of the nucleic acid, and the inventors therefore focused their attention on TdT and the like as potential enzymes for extension and reactive site introduction.

Furthermore, the inventors also focused their attention on the site-specific protein modification ability of transglutaminases (TGase) such as microbial transglutaminase (MTG) as a technique for covalently introducing a labeling compound into a reactive site-introduced nucleic acid that has undergone extension and reactive site introduction. TGase is an enzyme that catalyzes transacylation reactions, and is an enzyme that, for example, catalyzes the covalent binding of the γ-carboxamide group of specific Gln residues (Q) within a protein, and the ϵ-amino group of a lysine residue (K) or any of various primary amines. Using this TGase enables the creation of a protein-nucleic acid conjugate having an introduced labeling moiety such as a labeling enzyme. Because MTG and the like have superior substrate recognition properties, they can selectively crosslink the reactive site of the reactive site-introduced nucleic acid that has undergone extension and reactive site introduction and the reactive tag moiety of the detection enzyme or the like, and can introduce the labeling enzyme or the like with almost no loss in the activity of the enzyme.

Figure 3:
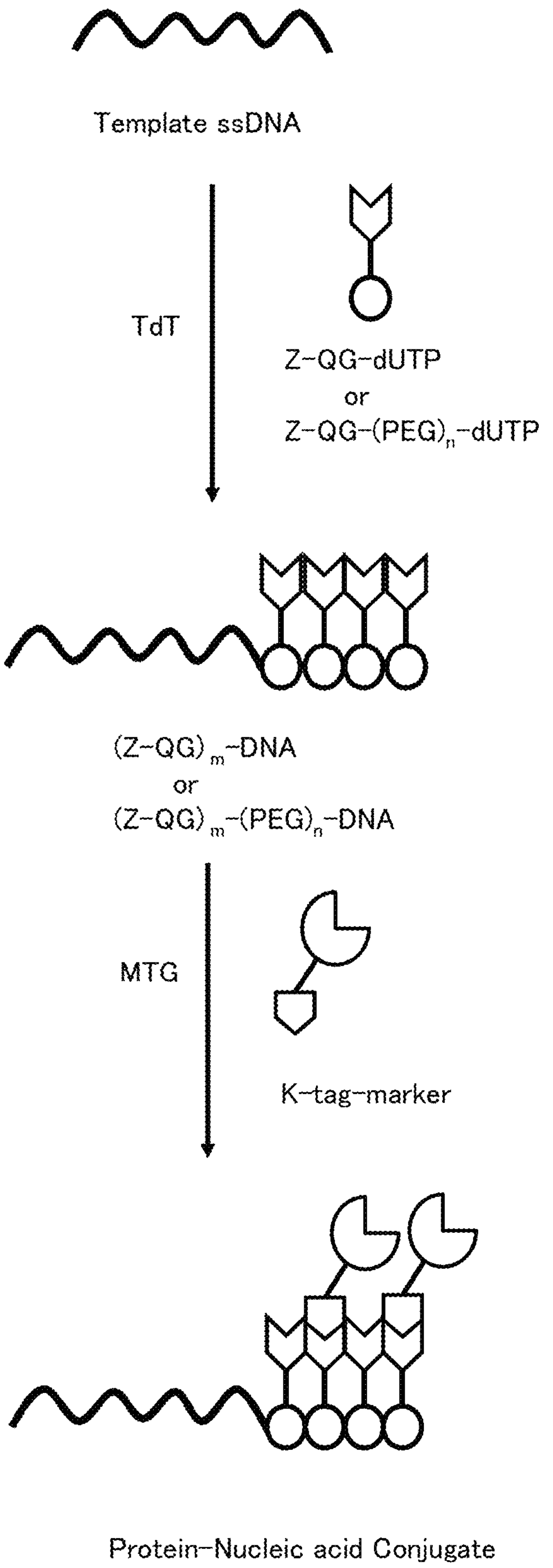
FIG. 3 is a schematic diagram illustrating one example of a method for preparing a protein-nucleic acid conjugate according to an embodiment of the present invention.

In a specific example, as illustrated in FIG. 1, by synthesizing a nucleotide derivative Z-QG-dUTP by binding Z-QG having a Gln residue that is recognized by TGase (MTG-recognizable Gln) to deoxyuridine triphosphate (dUTP), and then, as illustrated in FIG. 3, using TdT or the like to perform an extension reaction of the 3'-terminal of a template nucleic acid (such as a template DNA) to incorporate the Z-QG-dUTP, a $(Z\text{-}QG)_m$-DNA (reactive site-introduced nucleic acid) having an introduced TGase-recognizable Gln is prepared.

Subsequently, by using a TGase such as MTG to bind a labeling compound such as a labeling enzyme having an introduced TGase-recognizable Lys such as an MTG-recognizable Lys, a protein-nucleic acid conjugate having a ratio between the nucleic acid and the labeling moiety such as a labeling enzyme of 1:n (wherein n is an integer of 1 or greater) can be created.

Figure 4:
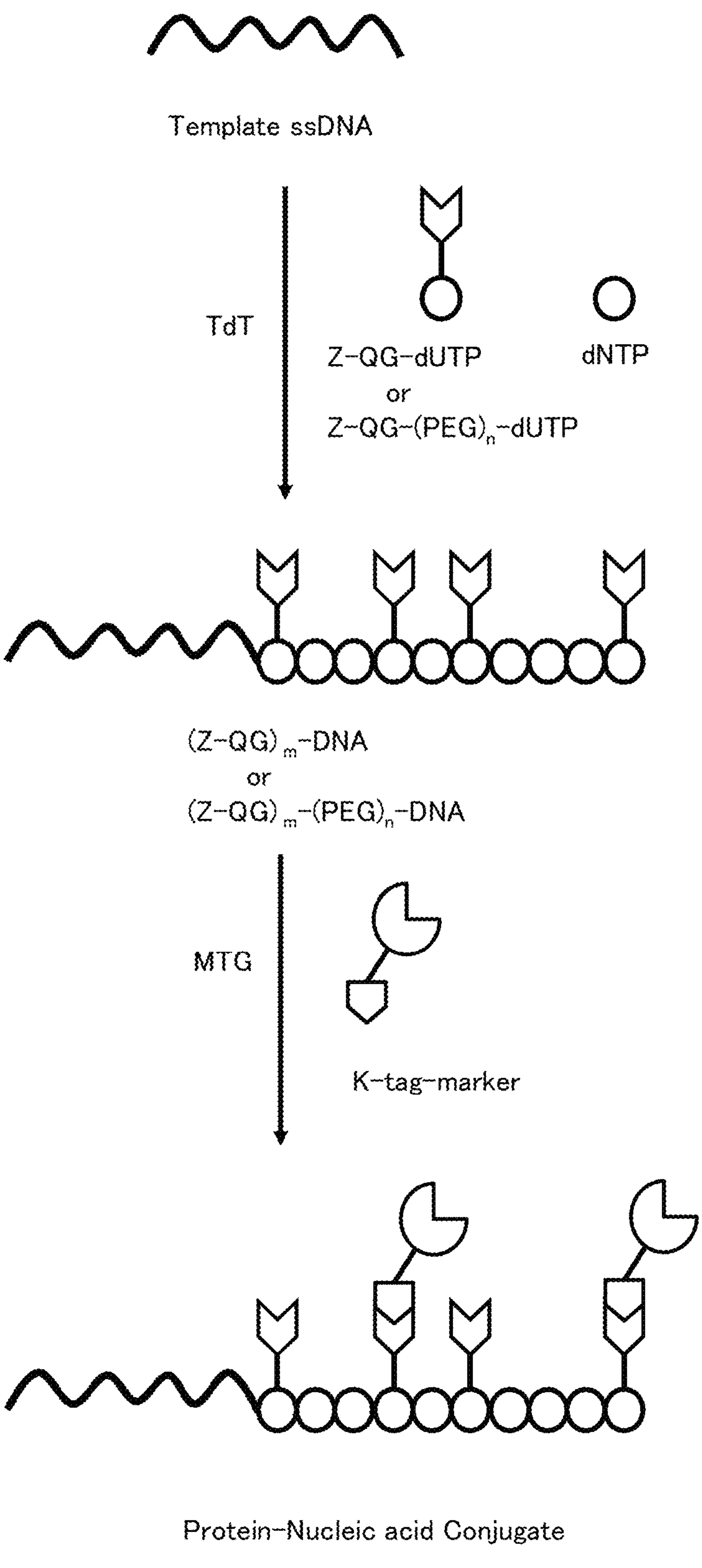
FIG. 4 is a schematic diagram illustrating one example of a method for preparing a protein-nucleic acid conjugate according to an embodiment of the present invention.

Further, as illustrated in FIG. 4, by using TdT or the like to incorporate dNTP together with Z-QG-dUTP when performing the extension reaction at the 3'-terminal of a template nucleic acid (such as a template DNA), a $(Z\text{-}QG)_m$-DNA (reactive site-introduced nucleic acid) having an introduced TGase-recognizable Gln is prepared. Subsequently, by using a TGase such as MTG to bind a labeling compound such as a labeling enzyme having an introduced TGase-recognizable Lys such as an MTG-recognizable Lys, a protein-nucleic acid conjugate having a ratio between the nucleic acid and the labeling moiety such as a labeling enzyme of 1:n (wherein n is an integer of 1 or greater) can be created.

Figure 2:
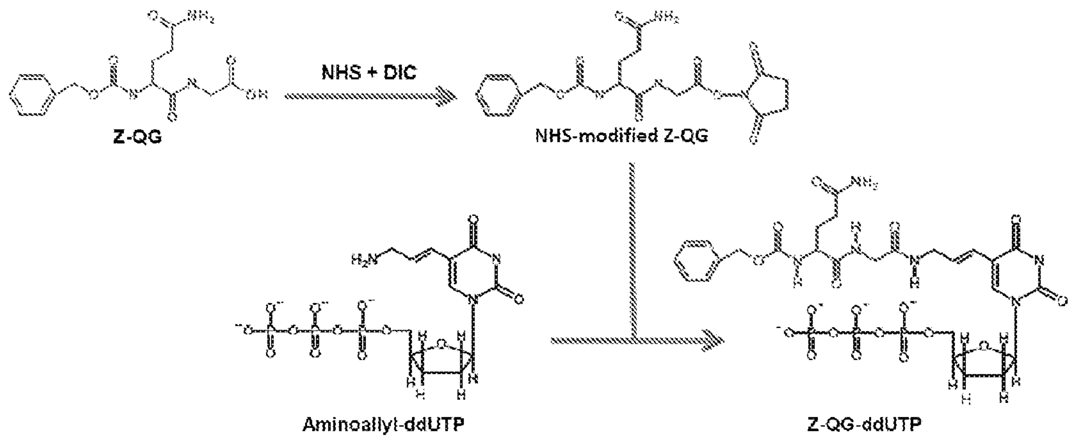
FIG. 2 is a diagram illustrating one example of a method for synthesizing Z-QG-ddUTP, which represents one example of a nucleotide derivative according to an embodiment of the present invention.
Figure 5:
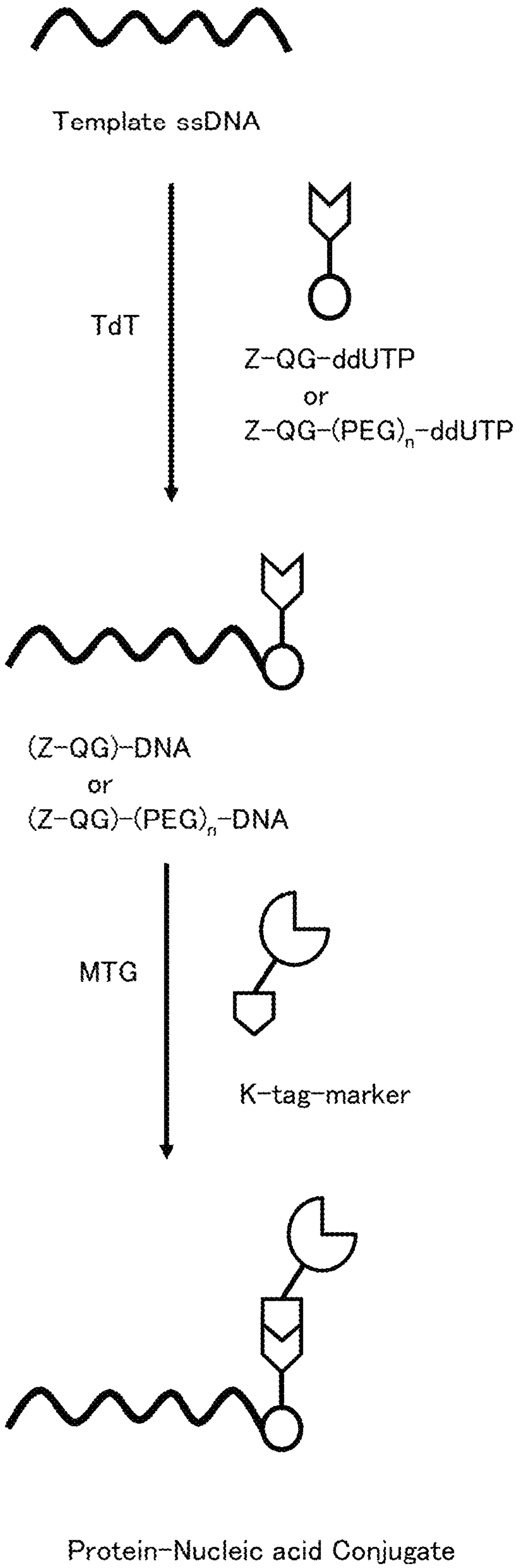
FIG. 5 is a schematic diagram illustrating one example of a method for preparing a protein-nucleic acid conjugate according to an embodiment of the present invention.

In a further example, as illustrated in FIG. 2, by synthesizing a nucleotide derivative z-QG-ddUTP by binding Z-QG to dideoxyuridine triphosphate (ddUTP), and then, as illustrated in FIG. 5, using TdT or the like to incorporate the Z-QG-ddUTP at the 3'-terminal of a template nucleic acid (such as a template DNA), a (Z-QG)-DNA (reactive site-introduced nucleic acid) having an introduced TGase-recognizable Gln is prepared. Subsequently, by using a TGase such as MTG to bind a labeling compound such as a labeling enzyme having an introduced TGase-recognizable Lys such as an MTG-recognizable Lys, a protein-nucleic acid conjugate having a ratio between the nucleic acid and the labeling moiety such as a labeling enzyme of 1:1 can be created.

Following binding to a target substance, this protein-nucleic acid conjugate can immediately undergo a detection reaction, and therefore compared with existing techniques, is expected to yield considerable operational simplification, a reduction in background, and a suppression of costs due to the use of the bulk enzyme microbial transglutaminase (MTG).

In FIGS. 3, 4 and 5, the Gln residue in the $(Z\text{-}QG)_m$-DNA (reactive site-introduced nucleic acid) and the Lys residue in the labeling compound may be reversed. In other words, by synthesizing a nucleoside triphosphate derivative having a Lys residue that is recognized by TGase (MTG-recognizable Lys), and then using TdT or the like to incorporate the nucleoside triphosphate derivative when performing an extension reaction at the 3'-terminal of a template nucleic acid, a reactive site-introduced nucleic acid having an introduced TGase-recognizable Lys is prepared. Subsequently, by using a TGase such as MTG to bind a labeling compound having an introduced TGase-recognizable Gln such as an MTG-recognizable Gln, a protein-nucleic acid conjugate having a ratio between the nucleic acid and the labeling moiety of 1:n (wherein n is an integer of 1 or greater) can be created.

In this manner, any effects on the target substance recognition site of the template nucleic acid, and on active sites such as the labeling moiety of the labeling enzyme are suppressed, meaning a labeling compound containing a site-specific labeling moiety can be introduced into the template nucleic acid.

There are no particular limitations on the 3'-terminal addition enzyme, provided it is an enzyme capable of adding a nucleotide to the 3'-terminal of the template nucleic acid, and examples include terminal deoxynucleotidyl transferase (TdT), Family A-type DNA polymerase, and poly(A) RNA polymerase. Among these, in terms of reaction efficiency and the like, TdT is preferred. TdT is an enzyme which randomly introduces a deoxynucleotide at the 3'-terminal of a nucleic acid in a non-template dependent manner. Family A-type DNA polymerase is an enzyme which introduces dATP at the 3'-terminal of a DNA in a non-template dependent manner, and poly(A) RNA polymerase is an enzyme which introduces ATP at the 3'-terminal of an RNA in a non-template dependent manner. The extension reaction using TdT or the like may be performed using conventional methods.

Examples of the template nucleic acid on which the 3'-terminal extension reaction is performed include DNA, PNA and RNA. There are no particular limitations on the sequence or length of the template nucleic acid. In terms of the length, because TdT or the like is to be bound, a length of at least 3 mer is preferable. Among such nucleic acids, from the viewpoint of enabling sequence-specific detection of the nucleic acid, nucleic acid probes formed from DNA, PNA or RNA having a complementary sequence to the target nucleic acid are desirable, and from the viewpoint of detecting molecules other than nucleic acids, nucleic acid aptamers formed from DNA or RNA are desirable. A nucleic acid aptamer is an oligonucleotide (DNA or RNA) which, due to its higher order structure, binds with superior affinity and specificity to a wide variety of target substances. A nucleic acid aptamer has binding specificity to organic small molecules or biopolymers or the like such as proteins.

Examples of the detection targets of nucleic acid aptamers include inorganic substances (such as zinc ions and nickel ions), organic small molecules (such as ATP), coenzymes (such as NAD), sugars (such as cellobiose), and proteins (such as thrombin and interferon-gamma).

The nucleoside triphosphate derivative according to the present embodiment has a glutamine (Gln) residue or a lysine (Lys) residue. Examples of nucleoside triphosphate derivatives having a glutamine (Gln) residue or a lysine (Lys) residue include uridine triphosphate (UTP) derivatives, adenosine triphosphate (ATP) derivatives, guanosine triphosphate (GTP) derivatives, cytidine triphosphate (CTP) derivatives, deoxyuridine triphosphate (dUTP) derivatives, deoxyadenosine triphosphate (dATP) derivatives, deoxyguanosine triphosphate (dGTP) derivatives and deoxycytidine triphosphate (dCTP) derivatives which have a glutamine (Gln) residue or a lysine (Lys) residue. In the nucleoside triphosphate derivative according to the present embodiment, the glutamine (Gln) residue or the lysine (Lys) residue is, for example, bound to a uracil, adenine, guanine or cytosine moiety, either directly or via a substituent.

These nucleoside triphosphate derivatives can be obtained from UTP, ATP, GTP, CTP, dUTP, dATP, dGTP, dCTP or various derivatives thereof.

Further, these nucleoside triphosphate derivatives may also be obtained from uridine, uridine monophosphate (UMP) and diphosphate (UDP), adenosine, adenosine monophosphate (AMP) and diphosphate (ADP), guanosine, guanosine monophosphate (GMP) and diphosphate (GDP), cytidine, cytidine monophosphate (CMP) and diphosphate (CDP), deoxyuridine, deoxyuridine monophosphate (dUMP) and diphosphate (dUDP), deoxyadenosine, deoxyadenosine monophosphate (dAMP) and diphosphate (dADP), deoxyguanosine, deoxyguanosine monophosphate (dGMP) and diphosphate (dGDP), deoxycytidine, deoxycytidine monophosphate (dCMP) and diphosphate (dCDP), as well as various derivatives of these compounds.

For example, the triphosphate derivatives of the above compounds can be obtained from uridine, adenosine, guanosine, cytidine, deoxyuridine, deoxyadenosine, deoxyguanosine or deoxycytidine by phosphorylation using a phosphorylation enzyme or the like (for example, see Seibutsu-kogaku kaishi (Journal of The Society for Biotechnology, Japan), 85(9), pp. 397 to 399 (2007), and Journal of Bioscience and Bioengineering, 87(6), pp. 732 to 738 (1999)), or by phosphorylation by phosphorus oxychloride in the presence of a proton sponge (for example, see Tetrahedron Letters, 29(36), pp. 4525 to 4528 (1988)).

The nucleoside triphosphate derivative according to the present embodiment may be, for example, a uridine triphosphate derivative represented by formula (2) below, having a Gln residue or a Lys residue that is recognizable by TGase.

(2)

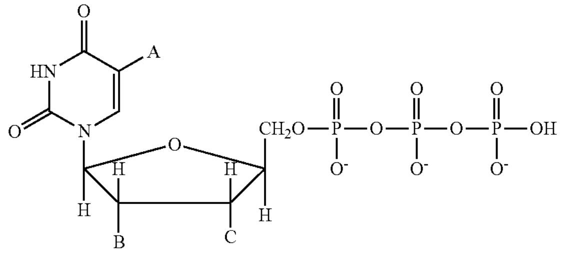

In formula (2), A represents a substituent having a glutamine (Gln) residue or a lysine (Lys) residue, B represents a hydrogen atom or a hydroxyl group, and C represents a hydrogen atom or a hydroxyl group.

The nucleoside triphosphate derivative according to the present embodiment may be, for example, an adenosine triphosphate derivative represented by formula (3) below, having a Gln residue or a Lys residue that is recognizable by TGase.

(3)

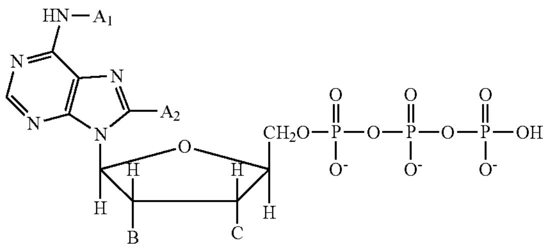

In formula (3), at least one of $A_1$ and $A_2$ represents a substituent having a glutamine (Gln) residue or a lysine (Lys) residue, with any remainder representing a hydrogen atom, B represents a hydrogen atom or a hydroxyl group, and C represents a hydrogen atom or a hydroxyl group.

The nucleoside triphosphate derivative according to the present embodiment may be, for example, a cytidine triphosphate derivative represented by formula (4) below, having a Gln residue or a Lys residue that is recognizable by TGase.

(4)

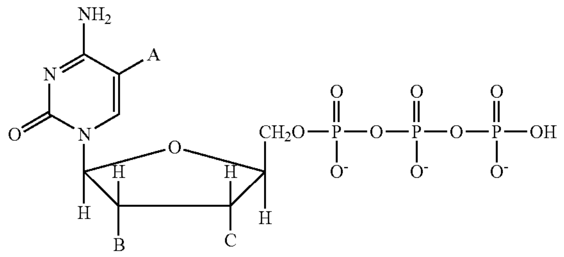

In formula (4), A represents a substituent having a glutamine (Gln) residue or a lysine (Lys) residue, B represents a hydrogen atom or a hydroxyl group, and C represents a hydrogen atom or a hydroxyl group.

The nucleoside triphosphate derivative according to the present embodiment may be, for example, a guanosine triphosphate derivative represented by formula (5) below, having a Gln residue or a Lys residue that is recognizable by TGase.

(5)

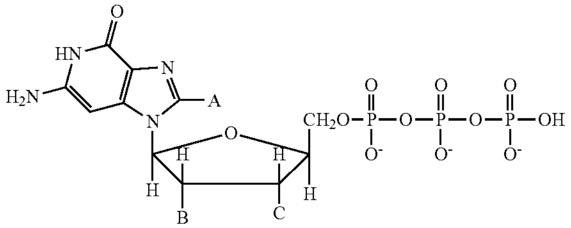

In formula (5), A represents a substituent having a glutamine (Gln) residue or a lysine (Lys) residue, B represents a hydrogen atom or a hydroxyl group, and C represents a hydrogen atom or a hydroxyl group.

There are no particular limitations on the substituent having a glutamine (Gin) residue or a lysine (Lys) residue represented by A, and examples include substituents comprising a linear, branched or cyclic, saturated or unsaturated alkyl group, aminoalkyl group, aryl group or heteroaryl group that has a glutamine (Gin) residue or a lysine (Lys) residue. The substituent may be selected with due consideration of factors such as the ease of synthesis.

The nucleoside triphosphate derivative according to the present embodiment is, for example, preferably a TGase substrate modified nucleotide derivative represented by formula (1) below, having a Gln residue or a Lys residue that is recognizable by TGase.

(1)

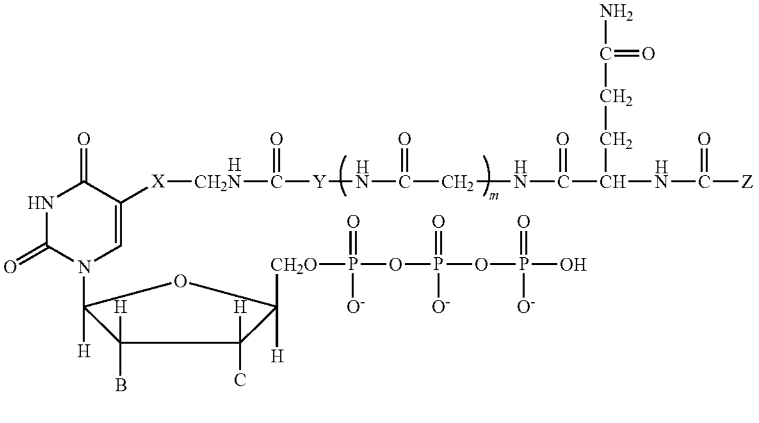

In formula (1), each of X and Y independently represents a divalent linking group, and Z represents a substituent. B represents a hydrogen atom or a hydroxyl group, C represents a hydrogen atom or a hydroxyl group, and m represents 0 or 1.

Examples of the bivalent linking groups represented by X and Y, which are mutually independent, include alkylene groups having a carbon number of 1 to 48 such as a methylene group, ethylene group, propylene group or butylene group, and alkenylene groups having a carbon number of 2 to 48 such as an ethenylene group, propenylene group or butenylene group. Of these, each of X and Y preferably independently represents an alkylene group having a carbon number of 1 to 48, an alkenylene group having a carbon number of 2 to 48, or an alkoxy group having a carbon number of 1 to 48, and those compounds in which X represents an ethenylene group and Y represents a methylene group are particularly desirable. X and Y may also be substituted with an ethenylene group or oxyalkylene group such as $-(C_2H_4O)_n-$ or $-(C_3H_6O)_n-$ (wherein n represents a repetition number, such that n=2, 4, 8, 12 or 24). An example of Y is $-(C_2H_4O)_n-C_2H_4-$.

Examples of the substituent represented by Z include alkyl groups having a carbon number of 1 to 48 such as a methyl group, ethyl group or propyl group, alkoxy groups having a carbon number of 1 to 48 such as a methoxy group, ethoxy group or propoxy group, aryl groups having a carbon number of 6 to 48 such as a phenyl group or naphthyl group, aryloxy groups having a carbon number of 6 to 48 such as a phenyloxy group, arylalkyl groups having a carbon number of 7 to 48 such as a benzyl group, and arylalkyloxy groups having a carbon number of 7 to 48 such as a benzyloxy group. Among these, Z is preferably an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48, and is more preferably a benzyloxy group. Z may also be substituted with a dinitrophenyl group or L-3,4-dihydroxyphenyl group or the like. Further, in combination with the above substituent represented by Y, at least one of Y and Z may be independently substituted with an amino acid other than Lys.

By appropriate selection of X and Y, the structure of the linker region that links the z-QG and UTP can be optimized. For example, by introducing a flexible linker region, access by enzymes and the like can be improved. Furthermore, by appropriate selection of Y and Z, the substrate peptide sequence can be optimized, for example enabling the affinity for enzymes and the like to be improved.

In those cases where microbial TGase (MTG) is used, the MTG-recognizable Gln residue preferably exists as benzyloxycarbonyl-L-glutamylglycine (Z-QG). Z-QG is preferable because it has a smaller molecular size than digoxigenin (DIG) or the like. In the nucleoside triphosphate derivative represented by formula (1), the nucleotide derivative in which X represents an ethenylene group, Y represents a methylene group, Z represents a benzyloxy group, B represents a hydrogen atom and C represents a hydroxyl group is the nucleotide derivative Z-QG-dUTP in which Z-QG is bound to dUTP. In the nucleoside triphosphate derivative represented by formula (1), the nucleotide derivative in which X represents an ethenylene group, Y represents a methylene group, Z represents a benzyloxy group, and B and C represent hydrogen atoms is the nucleotide derivative Z-QG-ddUTP in which Z-QG is bound to ddUTP. In the nucleoside triphosphate derivative represented by formula (1), the nucleotide derivative in which X represents an ethenylene group, Y represents $-(C_2H_4O)_4-C_2H_4-$, Z represents a benzyloxy group, B and C represent hydrogen atoms and m=1 is the nucleotide derivative Z-QG-$(PEG)_3$-ddUTP in which Z-QG-$(PEG)_3$- is bound to ddUTP. Further, it is preferable to select a nucleoside triphosphate derivative that does not contain both a TGase-recognizable Gln residue, and a Lys residue or primary amine. This is because if both residues exist, then there is a possibility that the TGase may cause self crosslinking, which may have an adverse effect on the yield of the targeted protein-nucleic acid conjugate.

Further, examples of good substrates for microbial TGase include peptides composed of amino acid sequences represented by LLQG (sequence number: 1), LAQG (sequence number: 2), LGQG (sequence number: 3), PLAQSH (sequence number: 4), FERQHMDS (sequence number: 5) or TEQKLISEEDL (sequence number: 6), or peptides composed of amino acid sequences represented by GLGQGGG (sequence number: 7), GFGQGGG (sequence number: 8), GVGQGGG (sequence number: 9), or GGLQGGG (sequence number: 10). Further, known examples of good substrates for guinea pig liver-derived TGase include benzyloxycarbonyl-L-glutamylphenylalanine (Z-QF), peptides composed of an amino acid sequence EAQQIVM (sequence number: 11), and peptides composed of amino acid sequences represented by GGGQLGG (sequence number: 12), GGGQVGG (sequence number: 13), GGGQRGG (sequence number: 14), GQQQLG (sequence number: 15), PNPQLPF (sequence number: 16) or PKPQQFM (sequence number: 17). Depending on the type of TGase used, the Gln residue that is recognizable by TGase may exist as one of these types of peptides.

In substrate peptides in which the N-terminal is a glycine (G), the N-terminal amino group can function as the TGase substrate, and therefore by-products caused by self crosslinking may occur. Accordingly, in the case of substrate peptides in which the N-terminal is a glycine (G), the peptide can be protected from becoming a TGase substrate by substituting the hydrogen atoms of the N-terminal amino group with an appropriate group, thereby ensuring that the desired linkage occurs. In this description, unless specifically stated otherwise, the expression "N-terminal protection" is used to describe this type of protection. It is known that the reactivity varies depending on the method employed for the N-terminal protection. Specifically, it is known that for mammal-derived TGase, protection by N-terminal acetylation of GQQQLG (namely, Ac-GQQQLG) or conversion of the N-terminal amino acid to DOPA (L-3,4-dihydroxyphenylalanine) (namely, DOPA-GQQQLG) results in increased reactivity. These types of protection examples may also be utilized in the present embodiment.

A method for preparing Z-QG-dUTP is illustrated in FIG. 1. This merely represents one example of a method for preparing a nucleoside triphosphate derivative according to the present embodiment, and the present invention is not limited to this example.

First, an N-hydroxysuccinimide (NHS) group or the like is introduced into benzyloxycarbonyl-L-glutamylglycine (Z-QG) to activate the molecule (NHS-modified Z-QG). Subsequently, a dUTP having an aminated substituent at the terminal such as aminoallyl-dUTP is condensed with the NHS-modified Z-QG, yielding Z-QG-dUTP. In a similar manner, Z-QG-ddUTP can be prepared as illustrated in FIG. 2.

Further, in addition to the above method in which the C-terminal carboxyl group is converted to an active ester, a method in which a functional group that exhibits high reactivity with amino groups is introduced into the peptide may also be used as a method of introducing a peptide having a TGase-recognizable Gln residue into dUTP. For example, if a substrate peptide that has undergone conversion to an aldehyde, acyl azide, sulfonyl chloride, epoxide, isocyanate or isothiocyanate can be prepared, then subsequent reaction of this substrate peptide with an aminated dUTP can be used to prepare a dUTP having a Gln residue that is recognizable by TGase. However, it is necessary that these reactive functional groups be introduced into the substrate peptide at positions that do not affect TGase recognition. In this regard, the method described above in which the carboxyl group of the C-terminal distant from the Gln residue is activated is the most desirable.

Purification of the Z-QG-dUTP can be performed by high performance liquid chromatography (HPLC) or gel permeation chromatography (GPC) or the like. Further, identification of the Z-QG-dUTP can be performed by MALDI TOF-MS, NMR and IR and the like. Further, HPLC can be used to confirm the product and determine the yield.

In the protein-nucleic acid conjugate, there are no particular limitations on the value of n in the ratio between the nucleic acid and the labeling moiety such as a labeling enzyme, provided that n is 1 or greater. The value of n may be altered as appropriate, but a larger value of n yields a higher detection sensitivity and is therefore preferred. However, if n is too large, then the efficiency of the binding such as the hybridization with the target substance may sometimes deteriorate.

Further, by using the methods described below, a plurality of protein-nucleic acid conjugates having different labeling moieties such as different labeling enzymes or different fluorescent dyes can be prepared.

(1) Changing the origin of the TGase (2) Changing the substrate specificity of the TGase In method (1), for example, UTP molecules or the like that have been modified with different substrate peptides may be prepared depending on the variety of TGase that is used.

In method (2), for example, an amino acid variation may be introduced into the TGase by protein engineering to change the substrate specificity. For example, MTG may be prepared in *E. coli* (for example, see Christian K. Marx, Thomas C. Hertel and Markus Pietzsch, Enzyme and Microbial Technology, volume 40, issue 6, 2 May 2007, pp. 1543 to 1550, "Soluble expression of a pro-transglutaminase from *Streptomyces mobaraensis* in *Escherichia coli*"), a variant library then generated, and the MTG variants exhibiting improved heat resistance then acquired (for example, see Christian K. Marx, Thomas C. Hertel and Markus Pietzsch, Journal of Biotechnology, volume 136, issues 3-4, 10 Sep. 2008, pp. 156 to 162, "Random mutagenesis of a recombinant microbial transglutaminase for the generation of thermostable and heat-sensitive variants").

When the present description states that "binding is performed using TGase", with the exception of special circumstances, this description means that the obtained linking moiety is generated as a result of the Lys residue and the Gln residue forming an ϵ-(γ-glutamyl) lysine bond.

In the present embodiment, the Lys residue that is recognizable by TGase may be a primary amine. In this description, a Lys residue is used as an example, but unless specifically stated otherwise, the description also applies to primary amines.

There are no particular limitations on the labeling compound having a glutamine (Gln) residue and containing a labeling moiety, or the labeling compound having a lysine (Lys) residue and containing a labeling moiety.

Examples of the labeling moiety include enzymes, fluorescent dyes, compounds containing a radioactive isotope, markers that can be detected magnetically (such as magnetic nanoparticles), markers that can be detected thermally (such as temperature-responsive polymers) and markers that can be detected electrically (such as polymers containing ferrocene sites), although from the viewpoints of detection sensitivity and handling, at least one of an enzyme and a fluorescent dye is preferable.

There are no particular limitations on the fluorescent dye, provided it is a material that emits fluorescence or phosphorescence in response to irradiation with ultraviolet light or visible light or the like of a selected wavelength. Examples of fluorescent dyes include fluorescein, rhodamine, dansyl and carbocyanine derivatives, whereas examples of fluorescent proteins include green fluorescent protein and variants thereof.

Examples of radioactive isotopes include deuterium ($^2$H), tritium ($^3$H) $^{10}$B, $^{11}$B, $^{13}$C, $^{15}$N and $^{18}$O.

It is thought that for TGase, a substrate that functions as a Lys residue donor has fewer structural restrictions than a substrate that functions as a Gln residue donor. Accordingly, there are cases where the labeling enzyme that is to be modified has a TGase-recognizable Lys residue from the beginning, and cases where a tag comprising a TGase-recognizable Lys residue is added to the enzyme.

The Lys residue (K) that is recognizable by TGase may exist as a peptide having an amino acid sequence represented by MKHKGS (sequence number: 18), MRHKGS (sequence number: 23), MRRKGS (sequence number: 24) or MHRKGS (sequence number: 25). Tagging with this type of peptide comprising a TGase-recognizable Lys residue can be used for the purpose of binding the labeling enzyme to a desired site on a protein, such as the C-terminal or N-terminal. Examples of other peptides comprising a TGase-recognizable Lys residue and their amino acid sequences include modified S-peptide (GSGMKETAAARFERAHMDSGS (sequence number: 19)), MGGSTKHKIPGGS (sequence number: 20), N-terminal glycines (N-terminal GGG, N-terminal GGGGG (sequence number: 21)), and MKHKGGGSGGGSGS (sequence number: 22) in which the linker region between N-terminal MKHKGS and the target protein has been extended.

Labeling enzymes having an added peptide comprising a TGase-recognizable Lys residue at the C-terminal or N-terminal can be prepared as recombinant proteins using genetic engineering techniques. Purification of such recombinant proteins in which a TGase substrate peptide tag has been introduced at the C-terminal or N-terminal can be conducted by gel permeation chromatography or the like, using a purification peptide tag added at the N-terminal or C-terminal respectively (for example, a (His)6-tag (hexahistidine tag)) (in order to avoid any deterioration in the reactivity of the TGase, the design should be made so that the purification peptide tag is introduced at a different terminal from the terminal containing the introduced substrate peptide tag). Further, confirmation of the amino acid sequence may be performed by using a DNA sequencer to confirm the gene sequence of the plasmid vector that codes the protein, or in the case of a substrate peptide introduced at the N-terminal, by direct identification by N-terminal analysis. Confirmation of the protein purification may be performed by SDS-PAGE or the like.

There are no particular limitations on the labeling enzyme, provided it has a property that enables detection to be performed using a coloration reaction or the like. Examples include alkaline phosphatase (AP), glutathione S-transferase (GST), luciferase and peroxidase. Of these, from the viewpoints of achieving high catalytic activity and good stability, an alkaline phosphatase or peroxidase is preferred. From the viewpoint of facilitating introduction of a peptide tag, proteins that can be produced by genetic engineering are preferred.

When the protein-nucleic acid conjugate is used as a nucleic acid probe, and a hybridization is performed between the nucleic acid probe and the target substance, reaction may sometimes be performed under comparatively high temperature conditions (for example, 70° C. or higher) in order to achieve a more precise base sequence-specific double strand formation, and therefore if a mesophile-derived enzyme is used, loss of activity may be a concern. In such cases, an alkaline phosphatase derived from the hyperthermophile *Pyrococcus furiosus* (PfuAP) is preferred as the labeling enzyme.

Enzymes derived from hyperthermophiles are known to generally exhibit high levels of stability relative to organic solvents and heat, and are therefore preferred (for example, see H. Atomi, Current Opinion in Chemical Biology, 9, pp. 166 to 173 (2005)), and are also preferred in terms of being comparatively easy to prepare in large quantities using a *E. coli* host. When preparing a heat-resistant enzyme using a *E. coli* host, by subjecting the cell homogenate to a high-temperature treatment (for example, by holding at 80° C. for 30 minutes), substantially all of the contaminant protein derived from the *E. coli* can be precipitated, enabling a crude purification to be performed with comparative ease.

Hyperthermophiles are microbes that can grow in extreme environments in which most bio-organisms cannot survive, and therefore hyperthermophile-derived proteins exhibit extremely high levels of heat resistance. Moreover, not only do they exhibit excellent resistance to heat, but generally also have much higher resistance to denaturants, organic solvents and pH and the like than mesophile-derived enzymes. Accordingly, it is thought that by using PfuAP, a more precise double strand formation can be achieved with no loss of enzyme activity.

Further, in the protein-nucleic acid conjugate, the enzyme may be stable relative to organic solvents and heat. This type of high-stability enzyme can be obtained by screening from the natural world (for example, see Chemistry and Chemical Industry, vol. 61 (No. 6), pp. 571 to 575 (2008), Taku Uchiyama and Kentaro Miyazaki, Bioscience and Industry, vol. 66 (No. 5), pp. 234 to 239 (2008), and Noriyuki Dokyu, Bioscience and Industry, vol. 66 (No. 12), pp. 667 to 670 (2008)), or by techniques for increasing the stability using protein engineering (for example, see Hiroyasu Ogino, Bio Industry, vol. 25 (No. 7), pp. 16 to 23 (2008), and Kentaro Miyazaki, Bio Industry, vol. 25 (No. 7), pp. 52 to 58 (2008)). By using these techniques, even enzymes derived from mesophiles can be converted to enzymes that exhibit favorable organic solvent resistance and heat resistance.

Labeling compounds containing an introduced fluorescent dye moiety and having a lysine (Lys) residue can be prepared, for example, by introducing a diamine at a carboxyl group (for example, see G. T. Hermanson (1996), Bioconjugate Techniques, chapter 1, section 4.3, pp. 100 to 104, Academic Press, San Diego).

A variety of enzymes can be used as the transglutaminase (TGase). Currently known TGase varieties include those derived from mammals (guinea pig and human), invertebrates (insects, horseshoe crab, sea urchin), plants, bacteria and protists (myxomycetes), and in the case of human-derived TGase, eight isozymes have been discovered. An example of a preferred TGase for use in the present embodiment, particularly in terms of stability, ease of handling and bulk producibility, is microbial transglutaminase (MTG).

When MTG is used in the present embodiment, based on the expected MTG catalysis, the binding reaction between the labeling compound containing the labeling moiety such as a labeling enzyme having a Lys residue and the $(Z\text{-}QG)_m$-DNA is predicted to proceed in two stages, namely formation of an acyl-enzyme conjugate via a nucleophilic substitution reaction of the cysteine (Cys) residue that represents the MTG active center at the Gln of the $(Z\text{-}QG)_m$-DNA, and a subsequent elimination of the MTG via a nucleophilic substitution reaction at the acyl-enzyme conjugate by the Lys of the labeling compound.

In a preferred configuration of the present embodiment, the molar concentration ratio of the labeling compound having the TGase-recognizable Lys residue, relative to the $(Z\text{-}QG)_m$-DNA having the TGase-recognizable Gln residue is preferably 2 or greater, and is more preferably 5 or greater. When the abbreviated term "concentration ratio" is used in this description, unless specifically stated otherwise, the term refers to a ratio between molar concentrations. For example, the molar concentration ratio of NK14-PfuAP relative to $(Z\text{-}QG)_m$-DNA can also be expressed as [NK14-PfuAP]/[$(Z\text{-}QG)_m$-DNA].

[Preparation of NK14-PfuAP]

NK14-PfuAP is a structure in which an additional sequence composed of an amino acid 14 residue having the sequence MKHKGGGSGGGSGS is introduced at the PfuAP N-terminal and a purification tag is introduced at the C-terminal by genetic engineering. The expression vector for PfuAP was received from Professor Haruhiko Sakuraba of Kagawa University. During amplification of the PfuAP coding region by PCR, recombination with the protein expression vector pET22 was conducted so as to introduce both tags, and the *E. coli* BL21 was transformed. Following preculture and subsequent main culture in an LB medium containing ampicillin, the resulting transformant was collected by centrifugal separation, and then washed twice with 25 mM TBS. Following freezing and thawing of the thus obtained microbe, the cells were pulverized by an ultrasonic treatment, and then centrifugal separation was used to collect the soluble fraction. The hyperthermophile-derived PfuAP is stable even under high-temperature conditions, and therefore a crude purification was performed by treating the obtained cell-free extract at 80° C. for 30 minutes, thus precipitating other proteins. Following this crude purification, the supernatant was collected by centrifugal separation and filtration, and subsequently purified using a His-tag column. Following purification, the liquid was concentrated by ultrafiltration, a PD-10 column was used to substitute the solvent medium with 10 mM Tris-HCl (pH 8.0), and the sample was frozen and stored until testing.

Furthermore, in order to improve the amount of expression of the NK14-PfuAP in the *E. coli*, the expression vector of an NK14-PfuAP in which the base sequence has been altered in accordance with the *E. coli* codon usage frequency (accession number: AB479383, sequence number: 26) may be used. This expression vector was obtained by custom synthesis by Codon Devices, Inc. (http://www.codondevices.com). An appropriate restriction enzyme site was introduced at both terminals of the gene region for coding the NK14-PfuAP, these sites were used to achieve recombination with the protein expression vector pET22, and the *E. coli* BL21 was transformed by the resulting NK14-PfuAP expression vector. Following preculture in an LB medium containing ampicillin and subsequent main culture, the resulting transformant was collected by centrifugal separation, and then washed twice with 25 mM TBS. Following freezing and thawing of the thus obtained microbe, the cells were pulverized by an ultrasonic treatment, and then centrifugal separation was used to collect the soluble fraction. The hyperthermophile-derived PfuAP is stable even under high-temperature conditions, and therefore a crude purification was performed by treating the obtained cell-free extract at 80° C. for 30 minutes, thus precipitating other proteins. Following this crude purification, the supernatant was collected by centrifugal separation and filtration, and subsequently purified using a His-tag column. Following purification, the liquid was concentrated by ultrafiltration, a PD-10 column was used to substitute the solvent medium with 10 mM Tris-HCl (pH 8.0), and the sample was frozen and stored until testing.

[Preparation of NK14-BAP]

NK14-BAP is a structure in which an additional sequence composed of an amino acid 14 residue having the sequence MKHKGGGSGGGSGS is introduced at the N-terminal of a *E. coli*-derived alkaline phosphatase (BAP) by genetic engineering, and a purification tag is introduced at the C-terminal. The BAP plasmid vector was received from Associate Professor Hiroshi Ueda of Tokyo University. During amplification of the BAP coding region by PCR, recombination with the protein expression vector pET22 was conducted so as to introduce both tags, and the *E. coli* BL21 was transformed. Following preculture and subsequent main culture in an LB medium containing ampicillin, the resulting transformant was collected by centrifugal separation, and then washed twice with TBS (Tris Buffered Saline). Following freezing and thawing of the thus obtained microbe, the cells were pulverized by an ultrasonic treatment, and then centrifugal separation was used to collect the soluble fraction. Following filtering, the soluble fraction was purified using a His-tag column and size exclusion chromatography. Following purification, a PD-10 column was used to substitute the solvent medium with 5 mM Tris-HCl (pH 8.0), and the sample was frozen and stored until testing.

In those cases where MTG is used as the TGase in the binding reaction, then in addition to ensuring that the molar concentration ratio satisfies a specific range as described above, the reaction is preferably performed at a pH of 5.5 to 8.0 and at a temperature of 4 to 50° C. (for example, at room temperature (18 to 22° C.)). Under such conditions, a satisfactorily high reaction rate can be achieved within 12 hours, preferably within 6 hours, and more preferably within 3 hours.

<Method for Detecting Target Substance>

The method for detecting a target substance according to an embodiment of the present invention comprises binding, via the nucleic acid moieties, the above-mentioned protein-nucleic acid conjugate and a target substance that exists within a target material, and detecting the bound protein-nucleic acid conjugate via the labeling moiety.

One example of a method of using the protein-nucleic acid conjugate according to the present embodiment as a nucleic acid probe, and binding this probe to a target substance via the nucleic acid moieties is a hybridization method in which the nucleic acid moiety of the protein-nucleic acid conjugate and the target nucleic acid that exists within the target material are bound complementarily, whereas in order to use the protein-nucleic acid conjugate as a nucleic acid aptamer, the higher order structure adopted by the nucleic acid moiety of the protein-nucleic acid conjugate is used to recognize and bind to the three dimensional structure of the target substance. The conditions required for these binding reactions can be set as appropriate by a person skilled in the art.

The method for detecting a target nucleic acid according to the present embodiment can be used for purposes such as qualitative or quantitative analysis of the target substance, or identification, staining or localization or the like of the target substance.

Examples of the target substance include nucleic acids, organic dyes, amino acids, antibodies, antibiotics, peptides, proteins and vitamins.

In the method for detecting a target substance according to the present embodiment, a plurality of protein-nucleic acid conjugates having different labeling moieties such as different labeling enzymes or different fluorescent dyes may be prepared, enabling a plurality of target substances to be detected simultaneously.

<Other Methods for Using the Protein-Nucleic Acid Conjugate>

The protein-nucleic acid conjugate according to the present embodiment can be used in the methods described below. For example, the conjugate can be used in a method for binding a protein having pharmacological activity and an aptamer, wherein by combining, within the protein-nucleic acid conjugate, a protein that exhibits pharmacological activity with a nucleic acid aptamer having directivity toward a lesion site, the protein can be transported to the lesion site, thereby enhancing the efficacy.

Further, the protein-nucleic acid conjugate can also be used in a method for binding a protein and a synthetic molecule, wherein the above-mentioned protein-nucleic acid conjugate and a complementary nucleic acid moiety introduced into a synthetic molecule can be bound together, thereby hybridizing the protein and the synthetic molecule non-covalently.

EXAMPLES

A more detailed description of the present invention is presented below based on a series of examples and comparative examples, but the present invention is in no way limited by the following examples.

Example 1

<Synthesis and Purification of Z-QG-dUTP>

First, 100 mM of N,N'-diisopropylcarbodiimide (DIC), 100 mM of N-hydroxysuccinimide (NHS) and 50 mM of Z-QG were reacted for 20 hours at room temperature (approximately 18 to 22° C. on the day of preparation) in 4 mL of N,N-dimethylformamide (DMF), thus preparing NHS-modified Z-QG (50 mM). Meanwhile, 16 μL of a 10 mM Tris-HCl (pH 7.5) solution (manufactured by Ambion, Inc.) containing 50 mM of 5-(3-aminoallyl)-dUTP (hereinafter abbreviated as "aminoallyl-dUTP", manufactured by Sigma-Aldrich Co., Ltd.), 40 μL of a 200 mM boric acid buffer solution (pH 8.8), and 16 μL of sterilized water were mixed to prepare 80 μL of a 10 mM aminoallyl-dUTP solution. To this solution was added 80 μL of the NHS-modified Z-QG solution prepared above, and the mixture was reacted overnight at 25° C. Following completion of the reaction, a sample of the product was diluted 10-fold with Milli-Q, and purification was performed by HPLC (manufactured by JASCO Corporation, high-performance liquid chromatograph and pump: TRI ROTAR-V series, variable loop injector: model VL-613, ultraviolet-visible spectroscopic detector: model UVIDEC-100-IV) under the conditions shown in Table 1. Identification of the product was performed using a MALDI TOF-MS apparatus (Autoflex III, manufactured by Bruker Daltonics Corporation). At this time, 3-hydroxypicolinic acid (3-HPA) was used as a matrix.

TABLE 1

| HPLC Measurement Conditions | |
|---|---|
| Column | Inertsil ODS-3 (10 mm × 250 mm) |
| Solvent | A = 100 mM TEAA (pH 7.0), B = acetonitrile |
| Gradient | A = 98% → 88% (5 min) |
| | A = 88% → 73% (30 min) |
| | A = 73% → 63% (10 min) |
| | A = 63% → 98% (5 min) |
| Flow rate | 5.0 mL/min |
| Detection wavelength | 260 nm |

Following preparation of the Z-QG-dUTP, reverse phase HPLC revealed the appearance of a new peak on the hydrophobic side of the peak observed for aminoallyl-dUTP, and this peak was assumed to be Z-QG-dUTP. Accordingly, the peak at a retention time of 19.1 minutes was collected, and subsequent analysis by MALDI TOF-MS confirmed a peak at 841.46, which represents a good match with the theoretical molecular weight of 842.13, thus confirming synthesis of Z-QG-dUTP.

<Preparation of $(Z\text{-}QG)_m$-DNA>

Using a DIG Oligonucleotide Tailing Kit (#3 353 583, manufactured by Roche Holding AG), a 3'-terminal extension reaction was performed with TdT. One μL of Z-QG-dUTP (1 mM), 1 μL of dATP (10 mM), 1 μg of a DNA (ShhPCR amplification product (300 bp), sequence number: 27), 1 μL of TdT (400 U/μL), 4 μL of a 5× reaction buffer, 4 μL of $CoCl_2$ (25 mM) and sterilized water were mixed to yield a total of 20 μL, and the resulting mixture was incubated at 37° C. for 30 minutes. Subsequently, 2 μL of 0.2 M EDTA was added, and following purification using a QIAquick PCR purification kit (manufactured by Qiagen), the mixture was eluted with 30 μL of an EB buffer to obtain a $(Z\text{-}QG)_m$-DNA. The TdT reaction was checked by electrophoresis (electrophoresis conditions: 1×TAE, Agarose 4% (Kanto HC), EtBr staining, applying voltage 100 V, 40 min). The results are shown in FIG. 6(*a*).

Figure 6:
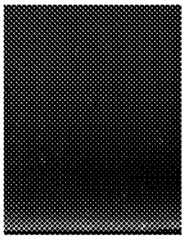
FIG. 6 includes (a) a diagram illustrating the results of electrophoresis with an agarose gel electrophoresis device when an extension reaction was performed using TdT in Example 1 ($(Z\text{-}QG)_m$-DNA), and (b) a diagram illustrating the results of electrophoresis with an agarose gel electrophoresis device when an extension reaction was performed using TdT in Example 1 ((Z-QG)-DNA).
Figure 6:
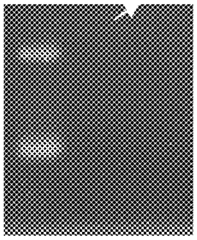

As is evident from FIG. 6(*a*), following the reaction with TdT, there was a large smeared shift to a higher molecular weight. It is thought that this indicates the introduction of a plurality of Gln at the 3'-terminal of the DNA.

<Preparation of $(PfuAP)_n$-DNA>

Using a LabellingONE alkaline phosphatase labeling kit (ALR-103, manufactured by Hitachi Aloka Medical, Ltd.), alkaline phosphatase labeling was performed. Specifically, 7.4 μL of the above $(Z\text{-}QG)_m$-DNA (estimated 27 ng/μL), 4 μL of a 10× reaction buffer, and 8.6 μL of sterilized water were mixed and subjected to heat denaturation at 95° C. for 5 minutes. After rapid cooling, 1 μL of PfuAP (8 mg/mL) and 1 μL of MTG were added, and following incubation at 40° C. for 3 hours, 2 μL of Stop solution was added to halt the reaction and obtain a $(PfuAP)_n$-DNA. The reaction was checked by electrophoresis (electrophoresis conditions: 1×TAE, Agarose 1.5% (Kanto LE), EtBr staining, applying voltage 100 V, 30 min). The results are shown in FIG. 7.

Figure 7:
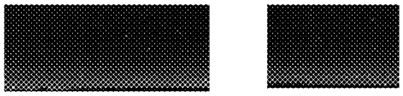
FIG. 7 is a diagram illustrating the results of electrophoresis with an agarose gel electrophoresis device when PfuAP labeling was performed using MTG in Example 1.

As is evident from FIG. 7, following the reaction, there was a shift to a higher molecular weight. It is thought that this indicates the labeling by the alkaline phosphatase.

<Z-QG-ddUTP>

A product synthesized by GeneACT, Inc. was used as the Z-QG-ddUTP.

Figure 17:
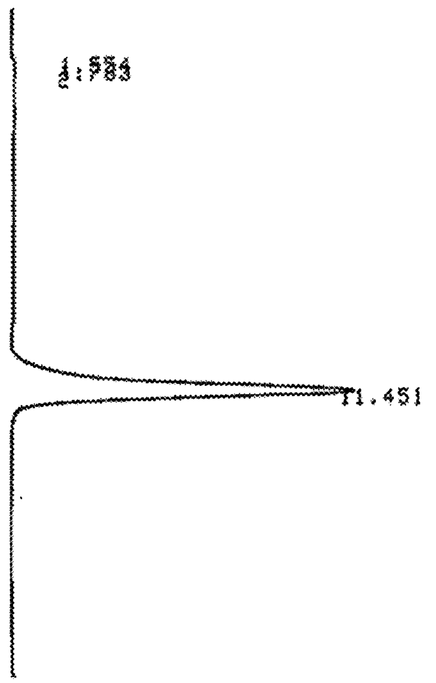
FIG. 17 is a diagram illustrating the results of reverse phase HPLC of Z-QG-ddUTP obtained in Example 1 of the present invention.
Figure 18:
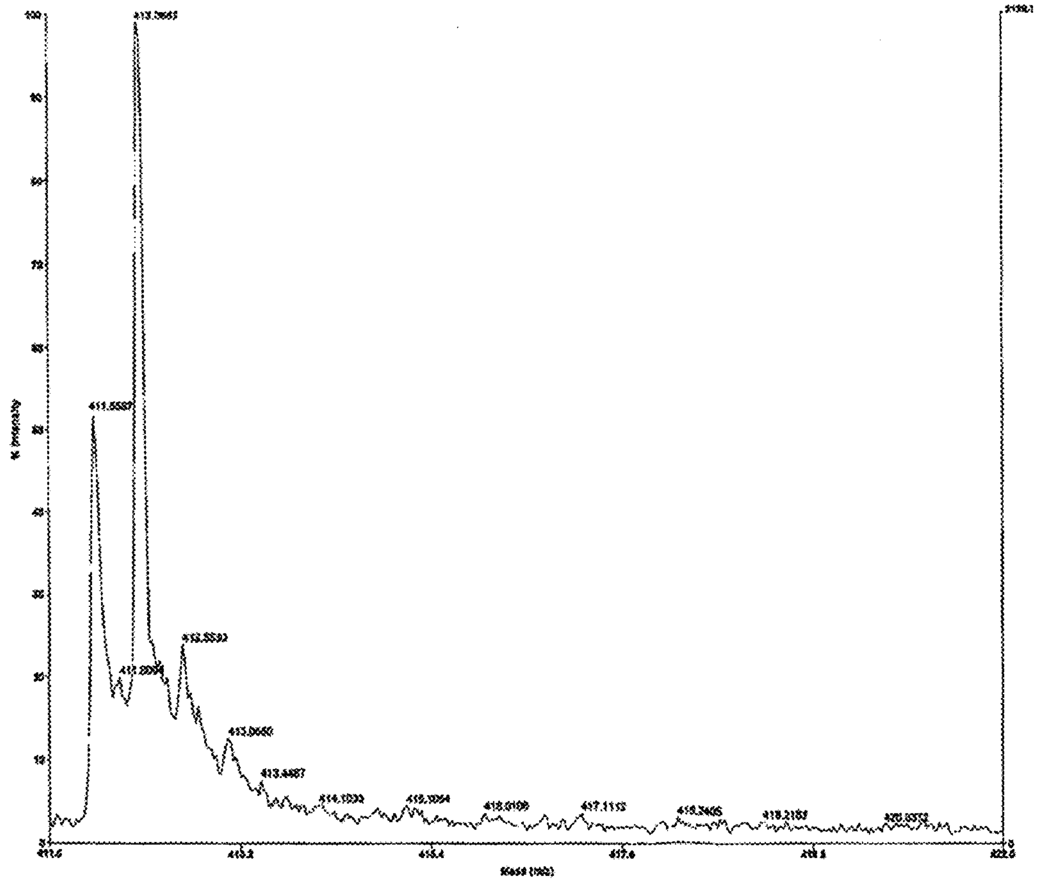
FIG. 18 is a diagram illustrating the results of MALDI TOF-MS analysis of Z-QG-ddUTP obtained in Example 1 of the present invention.

For the Z-QG-ddUTP, the results of performing reverse phase HPLC (column: COSMOSIL 5C-18MSII, 150×4.6 mm, buffer: 37% methanol in 20 mM potassium dihydrogen phosphate, 5 mM tetra-n-butylammonium hydrogen sulfate (pH 5.0), flow rate: 1.0 mL/min) are shown in FIG. 17. The component of the peak at a retention time of 11.45 minutes was analyzed by ESI-MS. As shown in FIG. 18, the results revealed a peak at 412.07 ($(M-2H)^{2-}$) (detected as a divalent ion peak (molecular weight×½−H)), which represents a good match with the theoretical molecular weight of 826.14, thus confirming the component as Z-QG-ddUTP.

<Preparation of (Z-QG)-DNA>

Using a DIG Oligonucleotide Tailing Kit (manufactured by Roche Holding AG), a 3'-terminal extension reaction was performed with TdT. One μL of Z-QG-ddUTP (1 mM), 1 μg of a DNA (Shh (300) PCR amplification product (300 bp)), 1 μL of TdT (400 U/μL), 4 μL of a 5× reaction buffer, 4 μL of $CoCl_2$ (25 mM) and sterilized water were mixed to yield a total of 20 μL, and the resulting mixture was incubated at 37° C. for 30 minutes. Subsequently, 2 μL of 0.2 M EDTA was added, and following purification using a QIAquick PCR purification kit (manufactured by Qiagen), the mixture was eluted with 30 μL of an EB buffer to obtain a (Z-QG)-DNA. The TdT reaction was checked by electrophoresis (electrophoresis conditions: 1×TAE, Agarose 4% (Kanto HC), EtBr staining, applying voltage 100 V, 50 min). The results are shown in FIG. 6(*b*).

As is evident from FIG. 6(*b*), following the reaction with TdT, there was a slight shift to a higher molecular weight. It is thought that this indicates the introduction of a single Gln at the 3'-terminal of the DNA.

<Preparation of (PfuAP)-DNA>

Using a LabellingONE alkaline phosphatase labeling kit (ALR-103, manufactured by Hitachi Aloka Medical, Ltd.), alkaline phosphatase labeling was performed. Specifically, 7.4 μL of the above (Z-QG)-DNA (estimated 27 ng/μL), 4 μL of a 10× reaction buffer, and 9.1 μL of sterilized water were mixed and subjected to heat denaturation at 95° C. for 5 minutes. After rapid cooling, 0.5 μL of PfuAP (8 mg/mL) and 1 μL of MTG were added, and following incubation at 40° C. for 3 hours, 2 μL of Stop solution was added to halt the reaction and obtain a (PfuAP)-DNA. The reaction was checked by electrophoresis (electrophoresis conditions: 1×TAE, Agarose 1.5% (Kanto LE), EtBr staining, applying voltage 100 V, 30 min). The results are shown in FIG. 7.

As is evident from FIG. 7, following the reaction, there was a shift to a higher molecular weight. It is thought that this indicates the labeling by the alkaline phosphatase.

<Evaluation of Detection Sensitivity by Dot Blot>

The detection sensitivity of each of the prepared PfuAP labeled nucleic acid probes was evaluated by dot blot. The various compositions and the protocol used during hybridization were as follows. Shh (sequence number: 27) was used as the target DNA. Further, Uromodulin (sequence number: 28) was used as a negative control.

Each target DNA was diluted in a stepwise manner with sterilized water, and 1 μL of each sample was spotted onto a membrane (Hybond N+, manufactured by GE Healthcare Corporation) and then crosslinked by UV to immobilize the DNA on the membrane. Subsequently, the membrane was transferred into 1.5 mL of a hybridization buffer (2 M urea, 0.5 M NaCl, 10 mM Tris-HCl (pH 9.5), 1 mg/mL Torula RNA, 1× Denhardt's Solution, 3% casein, 0.1% Triton X-100, 4% dextran sulfate), and a prehybridization was performed at 55° C. for 30 minutes. Then, the nucleic acid probe prepared in Example 1 or 2 ($(PfuAP)_n$-DNA, (PfuAP)-DNA) was added in 2 mL of a hybridization buffer (probe concentration: 10 ng/mL), and hybridization was performed at 55° C. for 16 hours.

Following hybridization, the membrane was rinsed once in 50 mL of a Wash I buffer (2 M urea, 100 mM Tris-HCl (pH 9.5), 150 mM NaCl, 0.1% Triton X-100), and was then transferred to another 50 mL of the Wash I buffer and washed by shaking for 30 minutes at 55° C. This operation was performed twice.

Subsequently, the membrane was washed at 25° C. for 5 minutes in 50 mL of a Wash II buffer (100 mM Tris-HCl (pH 9.5), 100 mM NaCl, 50 mM $MgCl_2$, 0.1% CHAPS). This operation was performed twice.

Using CDP-STAR (manufactured by Roche Holding AG) as a luminescent substrate, chemiluminescent reaction was performed at 25° C. for 2 hours, and the resulting state was captured using an image capture system (ChemiDoc XRS+, manufactured by Bio-Rad Laboratories, Inc.). The results are shown in FIG. 8.

Figure 8:
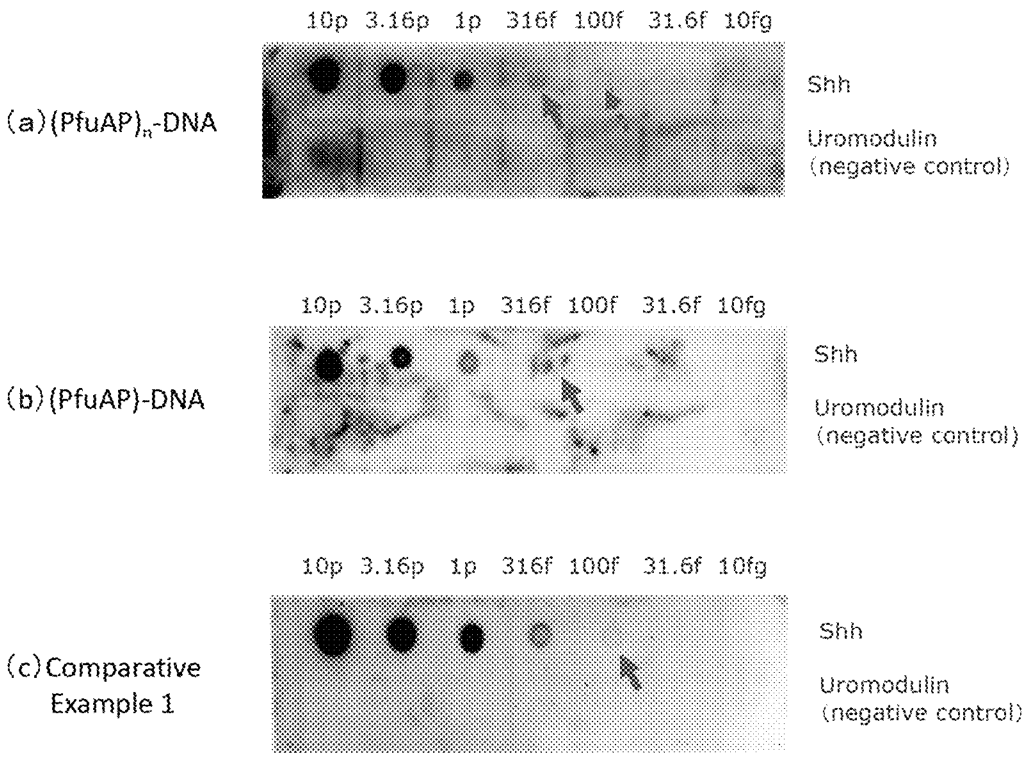
FIG. 8 includes (a) a diagram illustrating the results of a dot blot using a nucleic acid probe in Example 1 ($(PfuAP)_n$-DNA), (b) a diagram illustrating the results of a dot blot using a nucleic acid probe in Example 1 ((PfuAP)-DNA), and (c) a diagram illustrating the results of a dot blot using a nucleic acid probe in Example 1 (Comparative Example 1).

As is evident from FIG. 8, when the $(PfuAP)_n$-DNA (FIG. 8(*a*)) or the (PfuAP)-DNA (FIG. 8(*b*)) nucleic acid probe was used, dot signals were detected, indicating a detection ability as a nucleic acid probe. The $(PfuAP)_n$-DNA nucleic acid probe exhibited a signal sensitivity (of approximately 100 fg) similar to that of a typical labeling method by PCR using Z-QG-dUTP (Comparative Example 1, FIG. 8(*c*)). The (PfuAP)-DNA nucleic acid probe exhibited a signal sensitivity of approximately 316 fg.

Example 2

<Preparation of $(Z\text{-}QG)_m$-aptamer>

(Introduction of Z-QG-dUTP into DNA Aptamer Using TdT)

Z-QG-dUTP (final concentration 0.5 mM), a template DNA (DNA aptamer, 5'-FITC-GGTTGGTGTGGTTG-GTTTTTTTTTTTTTTT-3', 30 mer, reaction traced by fluorescent labeling, sequence number: 29) (final concentration 1 μM), TdT (final concentration 40 U/μL), a TdT reaction buffer (pH 6.6, composition: 200 mM potassium cacodylate, 25 mM Tris-HCl, 0.25 mg/mL BSA), $CoCl_2$ (final concentration 5 mM) and sterilized water were mixed, and the resulting mixture was incubated at 37° C. for 60 minutes. The mixture was sampled at 5, 10, 20, 30 and 60 minutes, and sufficient EDTA was added to produce a final concentration of 0.5 mM, thereby halting the reaction of each solution. The change over time in the TdT reaction was evaluated by polyacrylamide gel electrophoresis (PAGE) (electrophoresis conditions: 15% denatured polyacrylamide gel (containing urea 7 M), 280 V, 40 mA, 60 min, TBE buffer). The results are shown in FIG. 9.

Figure 9:
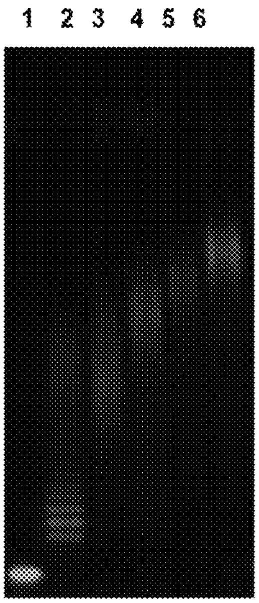
FIG. 9 is a diagram illustrating the change over time in electrophoresis results as the TdT reaction proceeds in Example 2.

As is evident from FIG. 9, the DNA (DNA aptamer) band shifts to a higher molecular weight as time elapses, and it is thought that with a [template DNA 1 μM]/[Z-QG-dUTP 0.5 mM] ratio, the TdT reaction saturates after approximately 60 minutes. TdT is introduced into the DNA until the nucleotide in the solution is disappeared. This is because TdT adds mononucleotides to the template by a partition method, and the reverse reaction does not occur, so that strand extension of the product by TdT reaction corresponds with the ratio of added nucleotides relative to the template. In the results shown in FIG. 9, the fact that the template DNA band has almost entirely disappeared is also thought to indicate that the reaction has been saturated because the Z-QG-dUTP has been added substantially equally to all the DNA, resulting in the disappearance of the Z-QG-dUTP.

(TdT Reaction in Mixture of Unmodified Nucleotide and Z-QG-dUTP)

When an extension reaction is performed using only Z-QG-dUTP, the Z-QG-dUTP molecule having a hydrophobic Z-QG exists in a continuous arrangement, and a hydrophobic interaction causes the Z-QG-dUTP molecules to cohere at the 3'-terminal, which may sometimes impair TdT access. Accordingly, an investigation was performed as to whether the introduction rate of Z-QG-dUTP could be enhanced by performing reaction with a mixture of an unmodified nucleotide and Z-QG-dUTP. Hence, dATP, dTTP, dCTP and dGTP were selected as examples of unmodified nucleotides representing the basic nucleotides that constitute nucleic acids, and extension reactions with TdT were performed simultaneously with these unmodified nucleotides and Z-QG-dUTP.

Z-QG-dUTP (final concentration 0.125 mM), each unmodified dNTP (final concentration 0.375 mM), a template DNA (DNA aptamer, the same as Example 2) (final concentration 1 μM), TdT (final concentration 40 U/μL), a TdT reaction buffer (pH 6.6), $CoCl_2$ (final concentration 5 mM) and sterilized water were mixed, and the resulting mixture was incubated at 37° C. for 60 minutes. Sufficient EDTA was then added to produce a final concentration of 0.2 mM, thereby halting the reaction of each solution. The TdT reaction was evaluated by polyacrylamide gel electrophoresis (PAGE) (electrophoresis conditions: 15% denatured polyacrylamide gel (containing urea 7 M), 280 V, 40 mA, 60 min, TBE buffer). The results are shown in FIG. 10.

Figure 10:
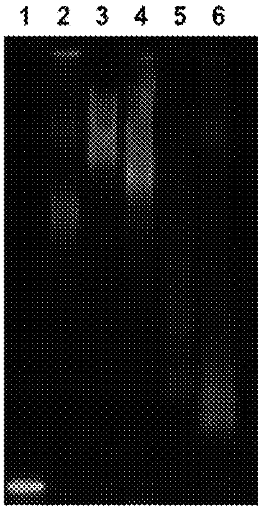
FIG. 10 is a diagram illustrating the electrophoresis results of introducing Z-QG-dUTP and various unmodified nucleotides by TdT reaction in Example 2.

As is evident from FIG. 10, the DNA aptamer reacted with Z-QG-dUTP (25%)+(dATP or dTTP (75%)) exhibited good extension. In the case of Z-QG-dUTP (25%)+(dCTP or dGTP (75%)), the extension was less than that observed for dATP or dTTP, and appeared to have undergone less extension than the Z-QG (100%) aptamer. In this manner, new bands were observed depending on the variety of nucleotide(s) used, confirming that the TdT substrate incorporation rates differed. The substrate incorporation rates in the TdT reaction exhibited a relationship represented by dATP≥dTTP >>dCTP>dGTP. The reason that the incorporation rates for dCTP and dGTP were low is thought to be due to that fact that the single strands of C and G readily form higher structures through interaction, thereby inhibiting access to the 3'-terminal, and increasing the likelihood of a halting of the extension reaction.

(Change of Substrate Mixing Ratio in TdT Reaction)

Under the same conditions as those described above for (TdT Reaction in Mixture of Unmodified Nucleotide and Z-QG-dUTP), TdT reactions were performed for various mixing ratios between Z-QG-dUTP and the dNTPs (dTTP or dATP). The proportion of Z-QG-dUTP was set to 0, 25, 50, 75 or 100%, and the change in the extension reaction was evaluated by PAGE (electrophoresis conditions: 15% denatured polyacrylamide gel (containing urea 7 M), 280 V, 40 mA, 60 min, TBE buffer). The results are shown in FIG. 11.

Figure 11:
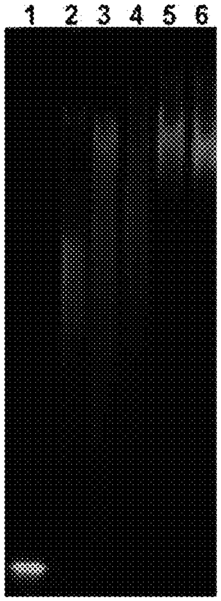
FIG. 11 is a diagram illustrating the electrophoresis results upon changing the substrate mixing ratio in the TdT reaction in Example 2.
Figure 11:
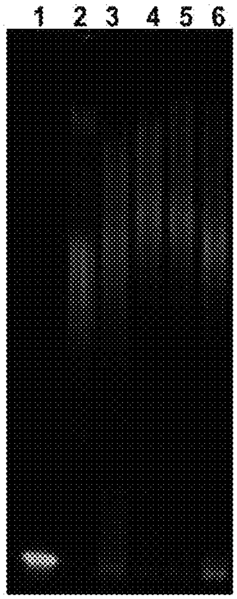

As is evident from FIG. 11, when the Z-QG-dUTP/dNTP mixing ratio was changed, in the case of the Z-QG-dUTP/dTTP combination, the band shifted to a higher molecular weight as the proportion of the Z-QG-dUTP was lowered, indicating that Z-QG-dUTP was difficult to incorporate with TdT. In the case of the Z-QG-dUTP/dATP combination, a shift to a higher molecular weight did not occur even when the proportion of Z-QG-dUTP was low, indicating that DNA aptamers of substantially the same strand length were being produced. It is thought that in the Z-QG-dUTP/dATP combination, the incorporation efficiency of Z-QG-dUTP was resistant to any decrease.

<Preparation 1 of $(BAP)_m$-Aptamers>

A $(Z\text{-}QG)_m$-aptamer prepared by TdT reaction was labeled with an alkaline phosphatase by an MTG reaction. Under conditions including the above-mentioned $(Z\text{-}QG)_m$-aptamer (final concentration 0.5 μM), NK14-BAP (amino acid sequence number: 30, base sequence number: 31) (final concentration 5.0 μM) and MTG (final concentration 0.01 U/mL), reaction was performed at 4° C. for one hour in a 200 mM Tris-HCl (pH 7.5) buffer solution. Evaluation of the reaction was performed by PAGE (electrophoresis conditions: Precast gel manufactured by Atto Corporation (15% polyacrylamide gel), 250 V, 20 mA, 80 min, Tris-Glycine buffer). The results are shown in FIG. 12.

Figure 12:
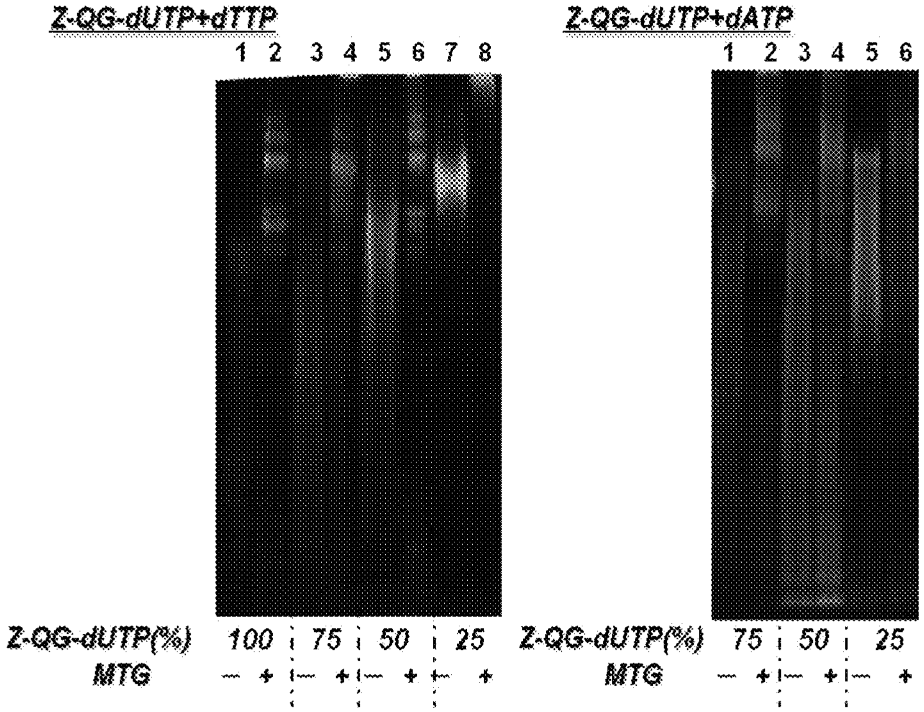
FIG. 12 is a diagram illustrating the electrophoresis results upon changing the substrate mixing ratio in the MTG reaction in Example 2.

As is evident from FIG. 12, new products were confirmed at the high molecular weight side in the lanes to which MTG was added. Moreover, in the cases of 100% Z-QG-dUTP and Z-QG-dUTP+dTTP, the original bands disappeared almost entirely. Accordingly, it was confirmed that MTG caused crosslinking between Z-QG and NK14-BAP in the DNA aptamers containing introduced Z-QG-dUTP, producing a $(BAP)_n$-aptamer conjugate.

<Evaluation of Thrombin Detection Ability of $(BAP)_m$-Aptamers>

(Effect of Linker Region Base)

Figure 13:
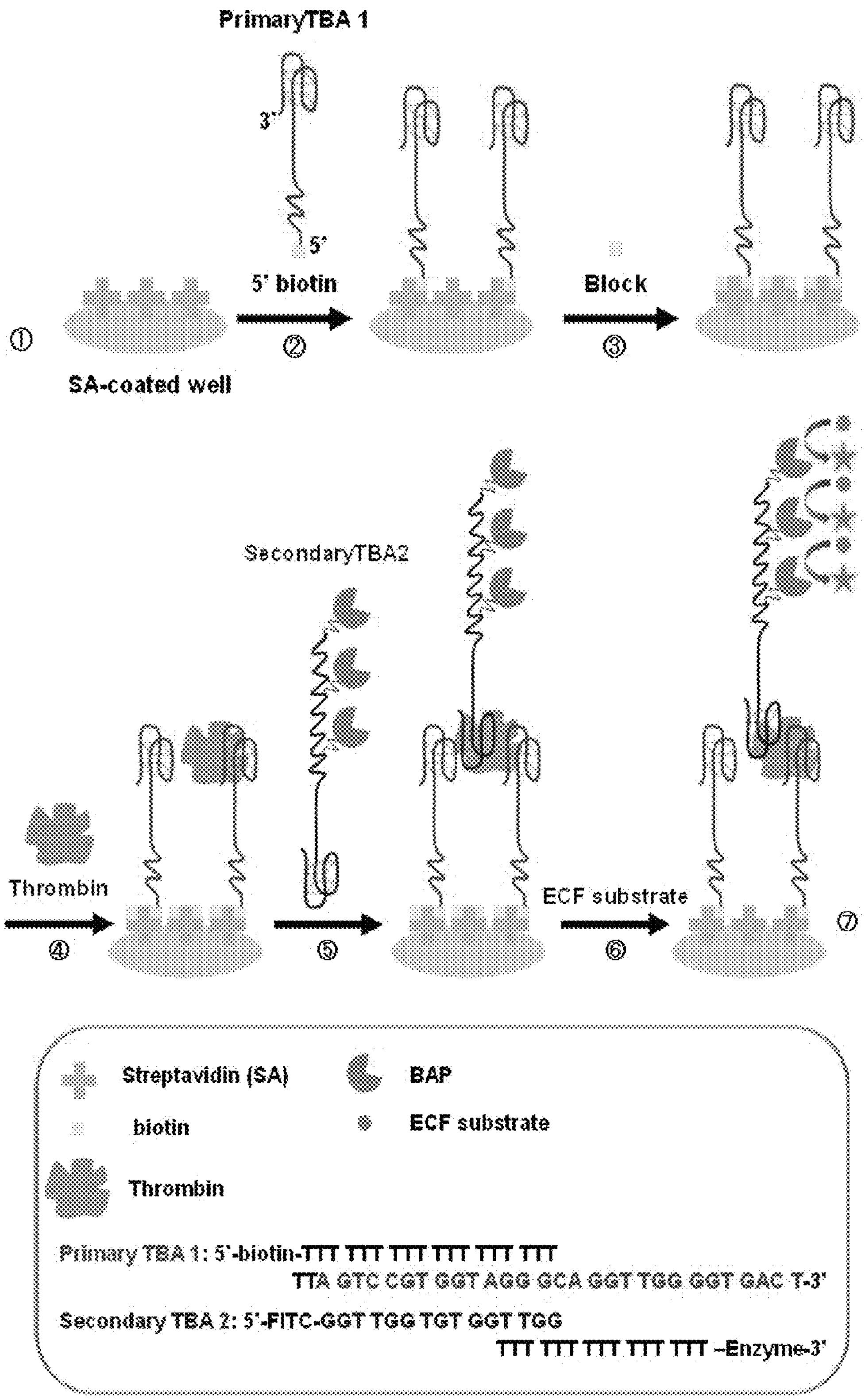
FIG. 13 is a schematic diagram illustrating one example of a procedure for detecting thrombin in Example 2.
Figure 14:
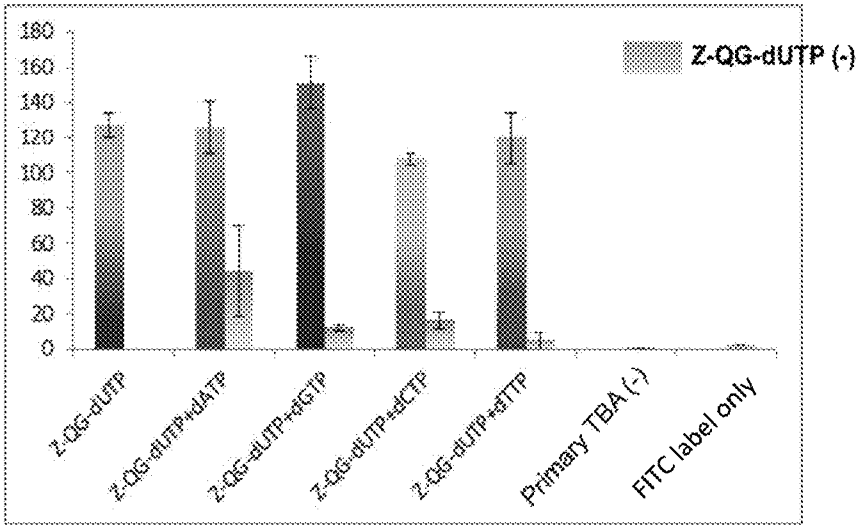
FIG. 14 is a diagram illustrating a comparison of the thrombin-binding abilities and signal amplifications of $(BAP)_n$-aptamers in Example 2.

Thrombin detection was performed in accordance with the operations shown in Table 2, using $(BAP)_m$-aptamers obtained by using MTG to crosslink BAP with DNA aptamers that had been extended with Z-QG-dUTP (25%) and various unmodified nucleotides (75%). The experimental procedure is shown in FIG. 13 and Table 2. Details of the buffer compositions are shown below. The results are shown in FIG. 14.

TABLE 2

Experimental Procedure for Thrombin Detection

| | Operation | Conditions |
|---|---|---|
| 1 | Preliminary washing | 37° C., TBST buffer (0.10% Tween 20) |
| 2 | TBA1 (0.5 μM, 100 μL/well) immobilization | 37° C., Buffer A, 1 hour |
| | Washing | 37° C., TBST buffer (0.10% Tween 20) |
| 3 | Blocking (0.1% BSA, 100 μL/well) | 37° C., TBS, 30 min |
| | Washing | 37° C., TBST buffer (0.10% Tween 20) |
| 4 | Thrombin (0.5 μM, 100 μL/well) immobilization | 4° C., Buffer B, 1 hour |
| | Washing | 37° C., TBST buffer (0.10% Tween 20) |
| 5 | TBA2 (0.2 μM, 100 μL/well) immobilization | 4° C., Buffer B, 1 hour |
| | Washing | 37° C., TBST buffer (0.10% Tween 20) |
| 6 | Enzyme reaction with ECF substrate (0.02 mM, 100 μL/well) | 37° C., NTM buffer, 30 min |
| 7 | Fluorescent intensity measurement | |

Buffer A: 5 mM Tris-HCl, 1 mM EDTA, 2 M NaCl (pH 7.5)

Buffer B: 50 mM Tris-HCl, 140 mM NaCl, 1 mM $MgCl_2$, 5 mM KCl, 0.1% BSA (pH 7.4)

NTM Buffer: 100 mM Tris-HCl, 100 mM NaCl, 50 mM $MgCl_2$ (pH 9.5)

As is evident from FIG. 14, the DNA aptamers prepared using a mixture of Z-QG-dUTP and various unmodified nucleotides and labeled with BAP each exhibited a higher fluorescent intensity than that of only an FITC label. This indicates that even when the DNA aptamer is labeled with an enzyme, the aptamer binds with thrombin with almost no deterioration in the thrombin-binding ability, and a signal amplification function due to the enzyme is achieved. In the case of the labeled DNA aptamers prepared using mixtures with dATP and dCTP, non-specific adsorption of BAP exists to some extent, but with the labeled DNA aptamers prepared using mixtures with dGTP and dTTP, almost no non-specific adsorption of BAP was observed. In particular, the DNA aptamer prepared using a mixture with dGTP exhibited a stronger signal than that observed with Z-QG-dUTP alone.

The reason for these results is thought to be that guanine undergoes almost no interaction with the thrombin-binding site of the DNA aptamer, namely the sequence including the guanine quadruplex. Similarly, dTTP undergoes almost no interaction with the guanine quadruplex, but because dTTP undergoes extension favorably, it is thought that the spacer becomes too long, resulting in a deterioration in the binding ability of the DNA aptamer, and a signal amplification that is not as great as that observed for the DNA aptamer prepared using a mixture with dGTP.

<Preparation 2 of $(BAP)_m$-Aptamers>

Figure 15:
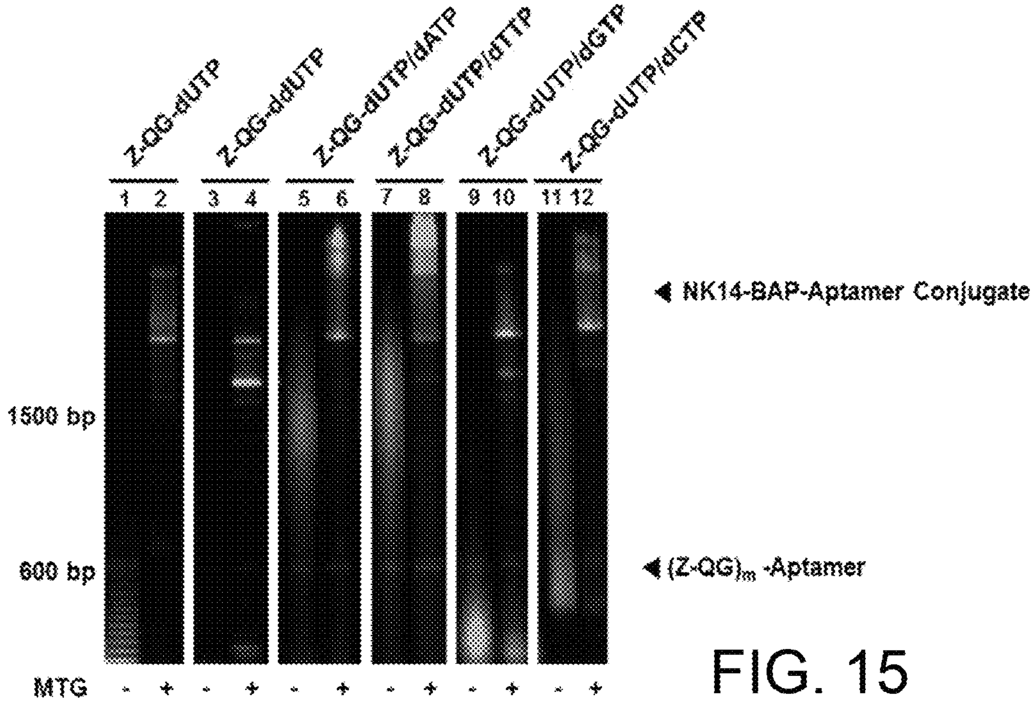
FIG. 15 is a diagram illustrating the electrophoresis results using different substrates in the microbial transglutaminase (MTG) reaction in Example 2.

A $(Z\text{-}QG)_m$-aptamer prepared by TdT reaction was labeled with an alkaline phosphatase by an MTG reaction in the same manner as that described above in (Preparation 1 of $(BAP)_m$-Aptamers). The results of PAGE analysis of the DNA aptamers following the MTG reaction are shown in FIG. 15. In FIG. 15, MTG(−) represents the DNA aptamer following TdT reaction, and MTG(+) represents the DNA aptamer following TdT reaction and subsequent MTG reaction. In the MTG(+) lane, each of the various DNA aptamers displays a shift to higher molecular weight, which is thought to indicate an increase in molecular weight as a result of BAP labeling. Further, in each of the aptamers extended by TdT reaction with a combination other than Z-QG-dUTP/dGTP, low-molecular weight TdT reaction products ((Z-QG)m-aptamers) disappeared almost completely, which is thought to indicate that BAP crosslinking using MTG had occurred with a reaction rate close to 100%. The bands in the vicinity of 600 bp are due to the gel background, and do not indicate the existence of FITC-DNA. Based on the above results, it was confirmed that all of the DNA aptamers underwent BAP labeling.

Further, comparison of the lanes following MTG reaction with Z-QG-dUTP and Z-QG-ddUTP revealed that the Z-QG-dUTP lane appeared on the higher molecular weight side, and therefore it is thought that a plurality of BAP molecules had crosslinked to the DNA aptamer that had been extended with Z-QG-dUTP. Based on similar thinking, it is thought that the DNA aptamers that had been modified using mixtures with each of the unmodified nucleotides also contain a plurality of crosslinked BAP molecules.

<Evaluation of Thrombin Detection Ability of $(BAP)_m$-Aptamers>

Figure 16:
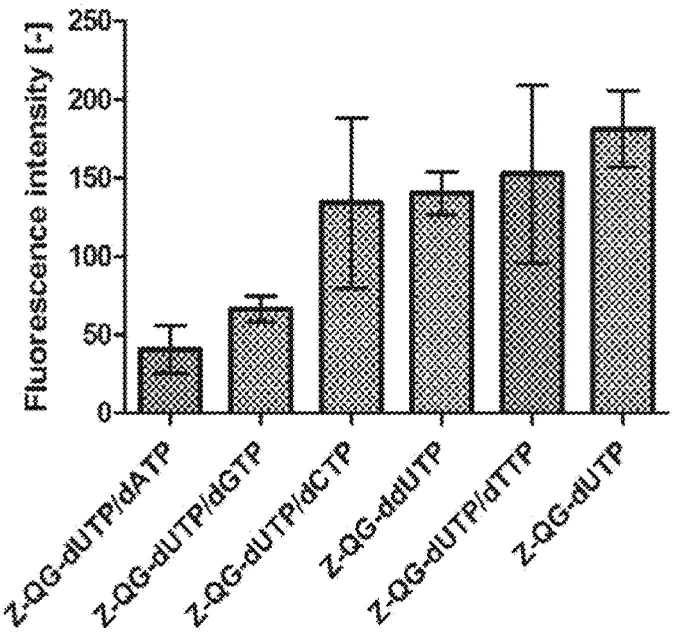
FIG. 16 is a diagram illustrating a comparison of the thrombin-binding abilities and signal amplifications with different substrates in Example 2.

The results of thrombin detection using the $(BAP)_m$-Aptamers prepared in the above-described (Preparation 2 of $(BAP)_m$-Aptamers) are shown in FIG. 16. The labeled DNA aptamers prepared by TdT reaction with Z-QG-dUTP and Z-QG-dUTP/dTTP achieved higher sensitivity detection than the single-labeled (Z-QG-ddUTP) DNA aptamer. First, this result confirmed an improvement in detection sensitivity due to a multiple labeling effect. Considering negative controls, if a comparison is made between no thrombin (Thrombin(−)) and a control containing the same concentration of BSA instead of thrombin (BSA(+)), then a fixed amount of non-specific adsorption occurred. If this is considered further, then the fact that some fluorescence is detected in the case of only the detection DNA aptamer (in this case the DNA aptamer prepared by labeling the aptamer extended with Z-QG-dUTP) is thought to indicate that a background occurs due to non-specific adsorption of the labeled DNA aptamer.

The correlation between the PAGE results of FIG. 15 reveals that Z-QG-dUTP and Z-QG-dUTP/dTTP, which exhibited bands on the high molecular weight side, achieved highly sensitive detection, and it is thought that this indicates that the labeling progresses further with increased molecular weight, resulting in improved detection sensitivity. The reason that the detection sensitivity of Z-QG-dUTP/dATP was low is thought to be due to the formation of a complementary strand by the thymine linker region and the adenine extension region, resulting in a deterioration in the binding ability of the DNA aptamer. Z-QG-dUTP/dGTP also displayed a small mobility shift in PAGE result, and the fact that the MTG reaction efficiency was also low indicates that the BAP labeling is insufficient, resulting in a lower detection sensitivity. There is a possibility that this type of decrease in reaction efficiency is due to an inhibition of substrate recognition by MTG and TdT due to the formation of a guanine quadruplex.

Example 3

<Preparation of (Z-QG)-Aptamer>

(Introduction of Z-QG-ddUTP into Aptamer by TdT)

Z-QG-ddUTP (final concentration 0.05 mM), a template DNA (the same DNA aptamer as Example 2) (final concentration 5 μM), TdT (final concentration 40 U/μL), a TdT reaction buffer (pH 6.6), $CoCl_2$ (final concentration 5 mM) and sterilized water were mixed, and the resulting mixture was incubated at 37° C. for 60 minutes. Following completion of the reaction, a heat treatment was performed at 94° C. for 15 minutes, and the solution was then cooled rapidly to halt the reaction. The reaction solution was purified using ProbeQuant G-50 Micro Columns to remove the unreacted Z-QG-ddUTP. The results of polyacrylamide gel electrophoresis (PAGE) are shown in FIG. 21 (electrophoresis conditions: 15% denatured polyacrylamide gel (containing urea 7 M), 280 V, 40 mA, 60 min, TBE buffer).

<Preparation of (BAP)-Aptamer>

The (Z-QG)-aptamer prepared by the TdT reaction was labeled with an alkaline phosphatase by an MTG reaction. Under conditions including the above-mentioned (Z-QG)-aptamer (final concentration 0.5 μM), NK14-BAP (final concentration 5.0 μM) and MTG (final concentration 0.1 U/mL), reaction was performed at 4° C. for 3 hours in a 200 mM Tris-HCl (pH 7.4) (final concentration 20 mM) buffer solution. Following completion of the reaction, sufficient NEM was added to achieve a concentration of 1 mM, and the MTG was deactivated. Evaluation of the reaction was performed by PAGE. The results are shown in FIG. 21.

Figure 21:
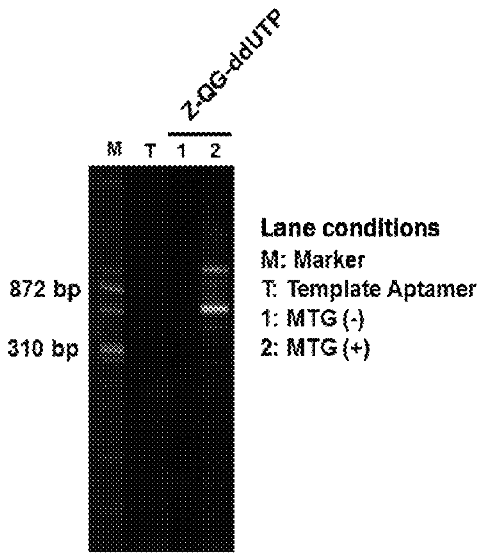
FIG. 21 is a diagram illustrating the results of electrophoresis after the TdT reaction and after the MTG reaction in Example 3.

In FIG. 21, the MTG(−) lane represents the DNA aptamer following TdT reaction, and the MTG(+) lane represents the DNA aptamer following TdT reaction and subsequent MTG reaction. The template DNA aptamer and TdT reaction products are washed away in the gel and are not visible, but high molecular weight side bands appeared in the MTG(+) lane, confirming a shift to higher molecular weight due to BAP labeling.

<Evaluation of Thrombin Detection Ability of (BAP)-Aptamer>

Thrombin detection was performed using an enzyme-linked aptamer assay (ELAA) method to evaluate the thrombin detection ability of the BAP single-labeled DNA aptamer ((BAP)-aptamer). In the ELAA method, thrombin was detected on a streptavidin-coated black plate (hereafter abbreviated as "the plate") using a biotinylated DNA aptamer as the immobilized ligand, and the (BAP)-aptamer as the detection ligand.

(Thrombin Detection Limit of (BAP)-Aptamer)

Figure 22:
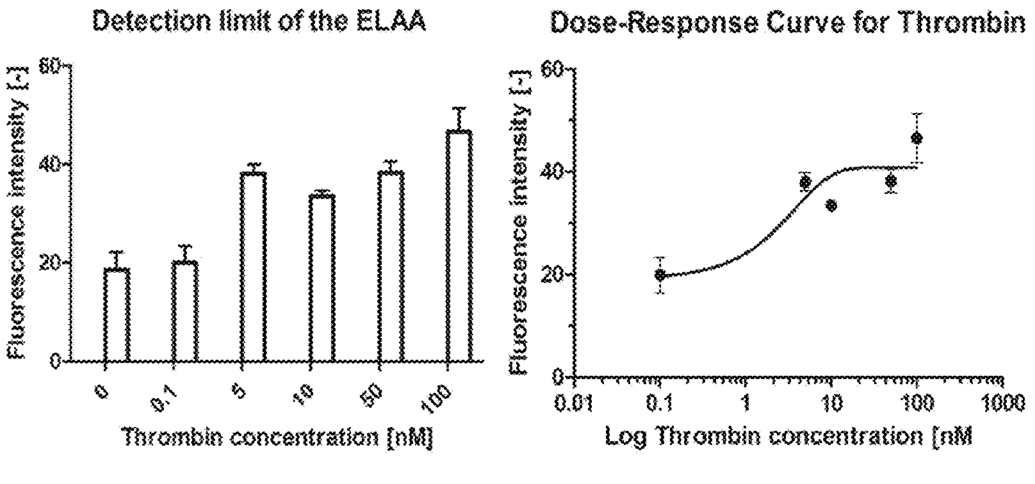
FIG. 22 includes (a) a diagram illustrating the results of the thrombin detection limit for a (BAP)-aptamer in Example 3, and (b) a diagram illustrating the dose-response curve.

Thrombin detection was performed by the ELAA method, under conditions including 100 μL/well of the biotinylated DNA aptamer (200 nM), 100 μL/well of a thrombin dilution series (100 nM, 50 nM, 10 nM, 1 nM, 0.1 nM, 0 nM), and 100 μL/well of the (BAP)-aptamer (50 nM). The experimental procedure was performed in accordance with Table 3, and the thrombin detection limit was calculated. The results for the thrombin detection limit of the (BAP)-aptamer are shown in FIG. 22.

TABLE 3

| | Operation | Conditions |
|---|---|---|
| 1 | Preliminary washing | RT 5 min, TBST buffer, 3 times/well |
| 2 | Biotinylated aptamer immobilization | 37° C. 1 hour, TBS, 100 μL/well |
| | Washing | RT 5 min, TBST buffer, 3 times/well |
| 3 | Blocking | 37° C. 30 min, TBS (1% BSA), 100 μL/well |
| | Washing | RT 5 min, TBST buffer, 3 times/well |
| 4 | Thrombin immobilization | 4° C. 1 hour, TBS, 100 μL/well |
| | Washing | RT 5 min, TBST buffer, 3 times/well |
| 5 | Detection aptamer immobilization | 4° C. 1 hour, TBS, 100 μL/well |
| | Washing | RT 5 min, TBST buffer, 3 times/well |
| 6 | Enzyme reaction with ECF substrate (0.02 mM) | 37° C. 1 hour, NTM buffer, 100 μL/well |
| 7 | Fluorescent intensity measurement | |

TBST buffer: TBS+0.10% Tween 20

NTM Buffer: 100 mM Tris-HCl, 100 mM NaCl, 50 mM $MgCl_2$ (pH 9.5)

Based on FIG. 22(*a*), the thrombin detection limit was 5 nM, and the dose-response curve (FIG. 22(*b*)) indicates a qualitative response down to the vicinity of 5 nM. It is thought these results represent satisfactory detection sensitivity as a single-labeled DNA aptamer.

Example 4

<Synthesis and Purification of Z-QG-$(PEG)_3$-ddUTP>

A product synthesized by GeneACT, Inc. was used as the Z-QG-$(PEG)_3$-ddUTP.

Figure 19:
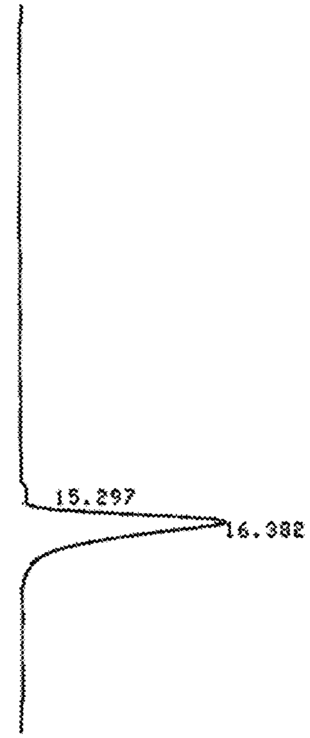
FIG. 19 is a diagram illustrating the results of reverse phase HPLC of Z-QG-$(PEG)_3$-ddUTP obtained in Example 4 of the present invention.
Figure 20:
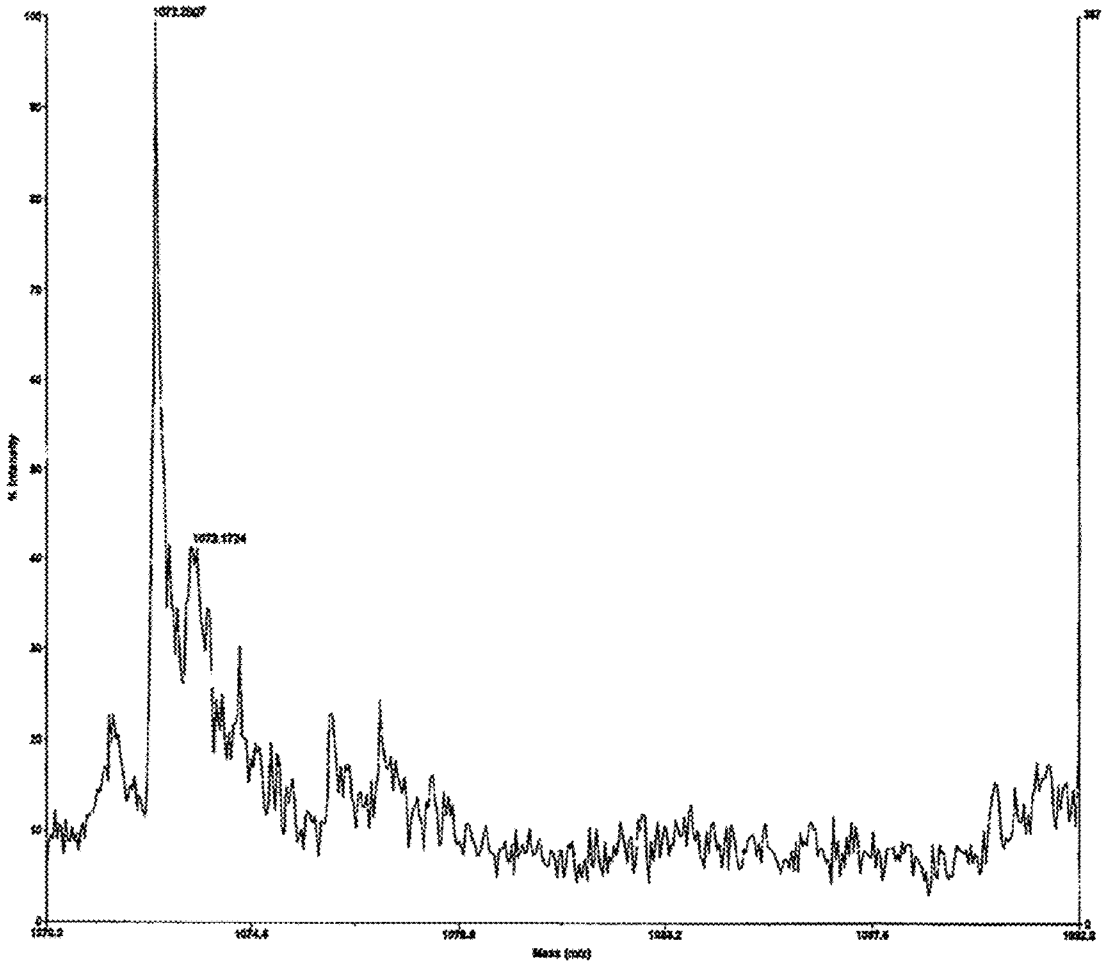
FIG. 20 is a diagram illustrating the results of MALDI TOF-MS analysis of Z-QG-$(PEG)_3$-ddUTP obtained in Example 4 of the present invention.

For the Z-QG-$(PEG)_3$-ddUTP, the results of performing reverse phase HPLC (column: COSMOSIL 5C-18MSII, 150×4.6 mm, buffer: 37% methanol in 20 mM potassium dihydrogen phosphate, 5 mM tetra-n-butylammonium hydrogen sulfate (pH 5.0), flow rate: 1.0 mL/min) are shown in FIG. 19. The component of the peak at a retention time of 16.38 minutes was analyzed by ESI-MS. As shown in FIG. 20, the results revealed a peak at 1072.28 ($(M-H)^-$), which represents a good match with the theoretical molecular weight of 1073.28 ($C_{38}H_{58}N_7O_{23}P_3$), thus confirming the component as Z-QG-$(PEG)_3$-ddUTP.

<Preparation of (Z-QG)-$(PEG)_3$-Aptamer>

(Introduction of Z-QG-$(PEG)_3$-ddUTP into DNA Aptamer by TdT)

Z-QG-$(PEG)_3$-ddUTP (final concentration 0.05 mM), a template DNA (the same DNA aptamer as Example 2) (final concentration 5 μM), TdT (final concentration 40 U/μL), a TdT reaction buffer (pH 6.6), $CoCl_2$ (final concentration 5 mM) and sterilized water were mixed, and the resulting mixture was incubated at 37° C. for 60 minutes. Following completion of the reaction, a heat treatment was performed at 94° C. for 15 minutes, and the solution was then cooled rapidly to halt the reaction. The reaction solution was purified using ProbeQuant G-50 Micro Columns to remove the unreacted Z-QG-$(PEG)_3$-ddUTP. The results of polyacrylamide gel electrophoresis (PAGE) are shown in FIG. 23 (electrophoresis conditions: 15% denatured polyacrylamide gel (containing urea 7 M), 280 V, 40 mA, 60 min, TBE buffer).

<Preparation of (BAP)-$(PEG)_3$-Aptamer>

The (Z-QG)-$(PEG)_3$-aptamer prepared by the TdT reaction was labeled with an alkaline phosphatase by an MTG reaction. Under conditions including the above-mentioned (Z-QG)-$(PEG)_3$-aptamer (final concentration 0.5 μM), NK14-BAP (final concentration 5.0 μM) and MTG (final concentration 0.1 U/mL), reaction was performed at 4° C. for 3 hours in a 200 mM Tris-HCl (pH 7.4) (final concentration 20 mM) buffer solution. Following completion of the reaction, sufficient NEM was added to achieve a concentration of 1 mM, and the MTG was deactivated. Evaluation of the reaction was performed by PAGE. The results are shown in FIG. 23.

Figure 23:
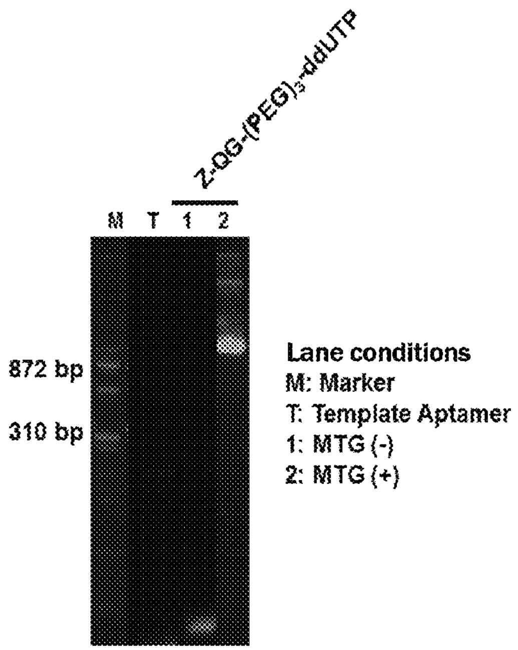
FIG. 23 is a diagram illustrating the results of electrophoresis after the TdT reaction and after the MTG reaction in Example 4.

In FIG. 23, the MTG(−) lane represents the DNA aptamer following TdT reaction, and the MTG(+) lane represents the DNA aptamer following TdT reaction and subsequent MTG reaction. Compared with the lanes for the template DNA aptamer and the TdT reaction product, high molecular weight side bands appeared in the MTG(+) lane, confirming a shift to higher molecular weight due to BAP labeling.

<Evaluation of Thrombin Detection Ability of (BAP)-$(PEG)_3$-Aptamer>

(Thrombin Detection Limit of (BAP)-$(PEG)_3$-Aptamer)

Thrombin detection was performed by the ELAA method, under conditions including 100 μL/well of the biotinylated DNA aptamer (200 nM), 100 μL/well of a thrombin dilution series (100 nM, 50 nM, 10 nM, 1 nM, 0.1 nM, 0 nM), and 100 μL/well of the (BAP)-$(PEG)_3$-aptamer (50 nM). The experimental procedure was performed in accordance with Table 3, and the thrombin detection limit was calculated. The results for the thrombin detection limit of the (BAP)-$(PEG)_3$-aptamer are shown in FIG. 24.

Figure 24:
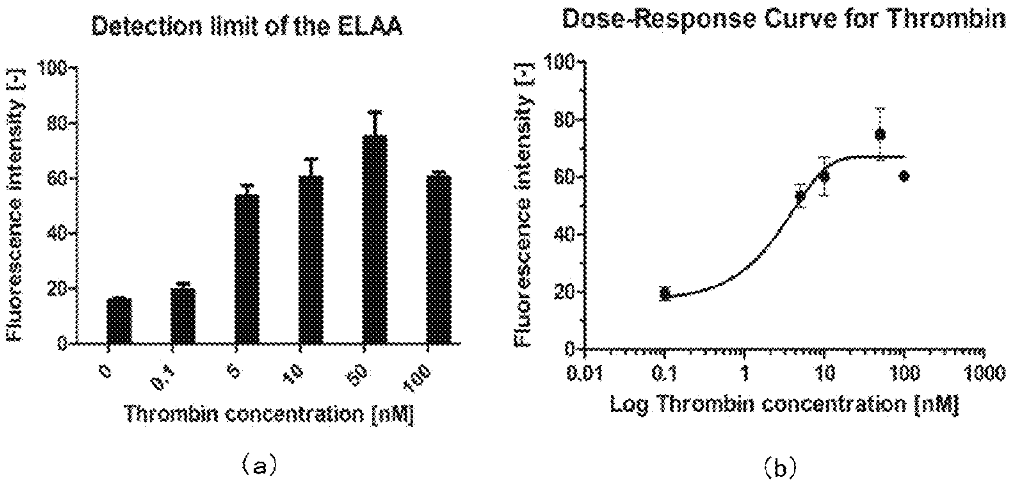
FIG. 24 includes (a) a diagram illustrating the results of the thrombin detection limit for a $(BAP)_n$-$(PEG)_3$-aptamer in Example 4, and (b) a diagram illustrating the dose-response curve.

Based on FIG. 24(*a*), the thrombin detection limit was 5 nM, and the dose-response curve (FIG. 24(*b*)) indicates a qualitative response down to the vicinity of 1 nM. In terms of the single-labeled detection limit, the qualitative range of the detection was broader than that for the (BAP)-aptamer, and a detection limit near 1 nM is superior to that of the DNA aptamer with no PEG linker. It is thought that the reason for this improved detection limit is that a moderation in electrostatic repulsion between DNA strands as a result of the PEG linker facilitates the binding of the detection DNA aptamer with the thrombin.

As described above, a protein-nucleic acid conjugate that can detect a target substance with good sensitivity was able to be created.

The invention claimed is:

1. A method for producing a protein-nucleic acid conjugate, the method comprising:

a 3'-terminal addition step of adding at least one nucleoside derivative to a 3'-terminal of a nucleic acid using a 3'-terminal addition enzyme which adds a nucleotide to a 3'-terminal of a nucleic acid, the nucleoside triphosphate derivative comprising a glutamine (Gln) residue, and a protein binding step of binding a protein to the glutamine (Gln) residue of the nucleoside triphosphate derivative, using a transglutaminase (TGase), the protein comprising a lysine (Lys) residue and a labeling moiety, wherein the nucleoside triphosphate derivative is represented by formula (1) shown below:

(1)

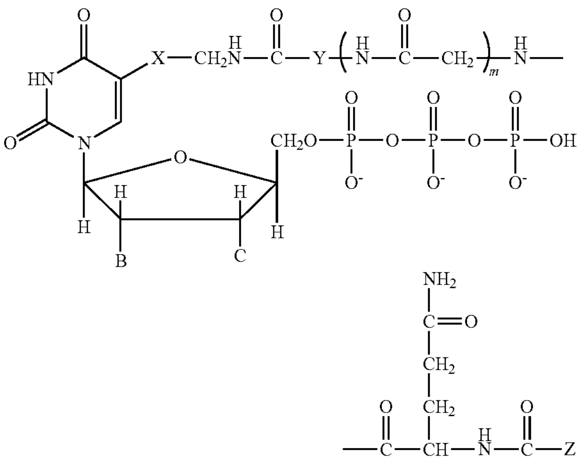

wherein each of X and Y independently represents an alkylene group having a carbon number of 1 to 48 or an alkenylene group having a carbon number of 2 to 48 which may be substituted with an ethenylene group, $-(C_2H_4O)_n-$ group or $-(C_3H_6O)_n-$ group, where n=2, 4, 8, 12 or 24, wherein Z represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48, which may be substituted with a dinitrophenyl group or an L-3,4-dihydroxyphenyl group, wherein at least one of Y and Z may be independently substituted with an amino acid other than Lys, wherein B represents a hydrogen atom or a hydroxyl group, wherein C represents a hydrogen atom or a hydroxyl group, wherein m represents 0 or 1, and wherein the 3'-terminal addition enzyme introduces the at least one nucleoside triphosphate derivate in a non-template dependent manner.

2. The method for producing a protein-nucleic acid conjugate according to claim 1, wherein the 3'-terminal addition enzyme is at least one of terminal deoxynucleotidyl transferase (TdT), Family A-type DNA polymerase, and poly(A) RNA polymerase.

3. The method for producing a protein-nucleic acid conjugate according to claim 1, wherein X represents an ethenylene group, Y represents a methylene group, and Z represents a benzyloxy group.

4. A method for detecting a target substance, the method comprising:

binding, via nucleic acid moieties a protein-nucleic acid conjugate, which is obtained by a method for producing a protein-nucleic acid conjugate comprising:

a 3'-terminal addition step of adding at least one nucleoside triphosphate derivative to a 3'-terminal of a nucleic acid using a 3'-terminal addition enzyme which adds a nucleotide to a 3'-terminal of a nucleic acid, the nucleoside triphosphate derivative comprising a glutamine (Gln) residue, and a protein binding step of binding a protein to the glutamine (Gln) residue of the nucleoside triphosphate derivative, using a transglutaminase (TGase) the protein comprising a lysine (Lys) residue and a labeling moiety, and a target substance which exists within a target material, and detecting the bound protein-nucleic acid conjugate by the labeling moiety, wherein the nucleoside triphosphate derivative is represented by formula (1) shown below:

(1)

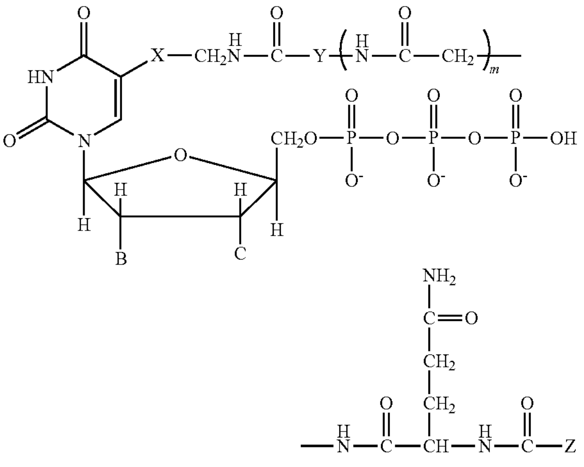

wherein each of X and Y independently represents an alkylene group having a carbon number of 1 to 48 or an alkenylene group having a carbon number of 2 to 48 which may be substituted with an ethenylene group, $-(C_2H_4O)_n-$ group or $-(C_3H_6O)$n- group where n=2, 4, 8, 12 or 24, wherein Z represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48, which may be substituted with a dinitrophenyl group or an L-3,4-dihydroxyphenyl group, wherein at least one of Y and Z may be independently substituted with an amino acid other than Lys, wherein B represents a hydrogen atom or a hydroxyl group, wherein C represents a hydrogen atom or a hydroxyl group, and wherein m represents 0 or 1, and wherein the 3'-terminal additional introduces the at least one nucleoside triphoshphate derivate in a non dependent manner.

5. The method for producing a protein-nucleic acid conjugate according to claim 1, wherein the 3'-terminal addition enzyme is terminal deoxynucleotidyl transferase (TdT).

6. The method for producing a protein-nucleic acid conjugate according to claim 1, wherein the 3'-terminal addition enzyme is Family A-type DNA polymerase.

7. The method for producing a protein-nucleic acid conjugate according to claim 1, wherein the 3'-terminal addition enzyme is poly(A) RNA polymerase.

8. The method for producing a protein-nucleic acid conjugate according to claim 4, wherein the 3'-terminal addition enzyme is at least one of terminal deoxynucleotidyl transferase (TdT), Family A-type DNA polymerase, and poly(A) RNA polymerase.

9. The method for producing a protein-nucleic acid conjugate according to claim 4, wherein X represents an ethenylene group, Y represents a methylene group, and Z represents a benzyloxy group.

10. The method for producing a protein-nucleic acid conjugate according to claim 4, wherein the 3'-terminal addition enzyme is terminal deoxynucleotidyl transferase (TdT).

11. The method for producing a protein-nucleic acid conjugate according to claim 4, wherein the 3'-terminal addition enzyme is Family A-type DNA polymerase.

12. The method for producing a protein-nucleic acid conjugate according to claim 4, wherein the 3'-terminal addition enzyme is poly(A) RNA polymerase.

* * * * *